US006864362B2

(12) United States Patent
Kinney

(10) Patent No.: US 6,864,362 B2
(45) Date of Patent: Mar. 8, 2005

(54) HYPOALLERGENIC TRANSGENIC SOYBEANS

(75) Inventor: Anthony J. Kinney, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/805,694

(22) Filed: Mar. 14, 2001

(65) Prior Publication Data

US 2003/0041350 A1 Feb. 27, 2003

Related U.S. Application Data

(60) Provisional application No. 60/189,823, filed on Mar. 16, 2000.

(51) Int. Cl.$^7$ ......................... C12N 15/82; C12N 12/29; C12N 15/11; A01H 5/00; A01H 5/10

(52) U.S. Cl. ..................... 536/23.1; 536/23.6; 800/285; 800/278; 800/290; 800/298; 800/312; 800/287; 435/468; 435/419; 435/320.1

(58) Field of Search .............................. 536/23.1, 23.6, 536/23.2; 800/285, 278, 290, 298, 312, 287, 295; 435/468, 419, 320.1

(56) References Cited

U.S. PATENT DOCUMENTS

| | | | |
|---|---|---|---|
| 3,488,770 A | 1/1970 | Atkinson | |
| 3,897,574 A | 7/1975 | Pass | |
| 4,454,804 A | 6/1984 | McCulloch | |
| 4,945,050 A | 7/1990 | Sanford et al. | |
| 5,107,065 A | 4/1992 | Shewmaker et al. | |
| 5,190,931 A | 3/1993 | Inouye | |
| 5,231,020 A | 7/1993 | Jorgensen et al. | |
| 5,283,323 A | 2/1994 | Berzofsky et al. | |
| 5,846,784 A | 12/1998 | Hitz | |

FOREIGN PATENT DOCUMENTS

| | | | | |
|---|---|---|---|---|
| EP | 0666034 A1 | 8/1995 | | |
| JP | 409121870 A | * 5/1997 | ........... | C12N/15/09 |
| WO | WO 93/11245 A1 | 6/1993 | | |
| WO | WO 94/11516 A1 | 5/1994 | | |
| WO | WO 97/47731 A2 | 12/1997 | | |
| WO | WO 99/53067 A | 10/1999 | | |
| WO | WO 99/54489 A | 10/1999 | | |

OTHER PUBLICATIONS

Finnegan and McElroy, 1994. Bio/technology 12: 883–888.*
Eshed et al (2001, Current Biology 11:1251–1260).*
Bryant (1989, Trends in Biotechnology 7(2):20–21).*
Martienssen (1998, PNAS 95:2021–2026).*
Moonan et al (2002, Journal of Virology 76(3):1339–1348.*
Warren Gish et al., Nature, vol. 3:266–271, Identification of protein coding regions by database similarity search.
Nobuhiro Ishibashi et al., Plant Mol. Biol., vol. 15:59–64, 1990, Stored mRNa in cotyledons of Vigna unguiculata seeds: nucleotide sequence of cloned cDNA for a stored mRNA and induction of its synthesis by precocious germination.
John Okuley et al., Plant Cell, vol. 6:147–158, 1994, Arabidopsis FAD2 Gene encodes the enzyme that is essential for polyunsaturated lipid synthesis.
Eliot M. Herman et al., Plant Phys., vol. 94:341–349, 1990, Apparent processing of a soybean oil body protein accompanies the onset of oil mobilization.
Mark D. Adams et al., Science, vol. 225:1651–1656, 1991, Complementary DNA sequencing: Expressed sequence tags and human genome project.
M. Araba et al., Andrzej Kalinski et al., Poultry Science, vol. 69:76–83, 1990, Evaluation of protein solubility as an indicator of overprocessing soybean meal.
Andrzej Kalinski et al., Journ. of Biol. Chem., vol. 267(17):12068–12076, 1992, A soybean vacuolar protein (P34) related to thiol proteases is synthesized as a glycoprotein precursor during seed maturation.
Andrzej Kalinski et al., Journ. of Biol. Chem., vol. 265(23):13843–13848, 1990, Molecular cloning of a protein associated with soybean seed oil bodies that is similar to thiol proteses of the papain family.
Steve L. Taylor et al., Nutrition Today, vol. 34:15–22, 1999, Food allergies and avoidance diets.
Anil Shirsat et al., Mol. Gen. Genet., vol. 215:326–331, 1989, Sequences responsible for the tissue specific promoter activity of a pea legumin gene in tobacco.
S. E. Radke et al., Theor. Appl. Genet., vol. 75:685–694, 1988, Transformation of *brassica napus* L. using *Agrobacterium tumefaciens*:developmentally regulated expression of a reintroduced napin gene.
R. N. Beachy et al., EMBO J., vol. 4(12):3047–3053, 1985, Accumulation and assembly of soybean beta–conglycinin in seeds of transformed petunia plants.
Yuji Ishida et al., Nature Biotech., vol. 14:745–750, 1996, High efficiency transformation of maize (*Zea mays* L.) mediated by *Agrobacterium tumefaciens*.
Joel Vandekerckhove et al., Bio/Technology, vol. 7:921–932, 1989, Enkephalins produced in transgenic plants using modified 2S seed storage proteins.

(List continued on next page.)

*Primary Examiner*—Phuong T. Bui
*Assistant Examiner*—Stuart F. Baum

(57) ABSTRACT

Hypoallergenic transgenic soybeans and recombinant expression constructs to lower soybean vacuolar protein, commonly know as P34, as well as other allergens are disclosed. Soybean protein products made from these hypoallergenic soybeans should be substantially free of the major soy allergen, P34, and, in addition, other minor soy allergens, such as, Gly m Bd 28K, alpha-subunit of beta-conglycinin, KSTI, Gly m2, Gly m 1A, Gly m 1B, rGLY m3 and glycinin G1.

5 Claims, 6 Drawing Sheets

OTHER PUBLICATIONS

National Center for Biotechnology Information General Identifier No. 112671, Oct. 1, 2000, Ishibashi, N. et al., Stored mRNA in cotyledons of Vigna unguiculata seeds: nucleotide sequence of cloned cDNA for a stored mRNA and induction of its synthesis by precocious germination.

National Center for Biotechnology Information General Identifier No. 4510397, Apr. 5, 2000, Lin. X. et al., Sequence and analysis of chromosome 2 of the plant *Arabidopsis thaliana*.

Xiaoying Lin et al., Nature, vol. 402:761–768, 1999, Sequence and analysis of chromosome 2 of the plant *Arabidopsis thaliana*.

National Center for Biotechnology Information General Identifier No. 1199562, Sep. 30, 1996, Kalinski, A. et al., Molecular cloning of a protein associated with soybean seed oil bodies that is similar to thiol proteases of the papain family.

National Center for Biotechnology Information General Identifier No. 5019731, Jun. 9, 1999, Gijzen, M. et al.

National Center for Biotechnology Information General Identifier No. 3021372, Nov. 15, 2000, RIHS, H.P. et al., IgE binding of the recombinant allergen soybean profilin (rGly m 3) is mediated by conformational epitopes.

National Center for Biotechnology Information General Identifier No. 3021374, Nov. 15, 2000, RIHS, H.P. et al., IgE binding of the recombinant allergen soybean profilin (rGly m 3) is mediated by conformational epitopes.

National Center for Biotechnology Information General Identifier No. 18614, Mar. 21, 1995, Negoro, T. et al., A cDNA clone encoding a glycinin A1a subunit precursor of soybean.

A. Wesley Burks, Jr. et al., J. Allerg. Clin. Immuno., vol. 81:1135–1142, 1988, Allergenicity of major component proteins of soybean determined by enzyme–linked immunosorbent assay (ELISA) and Immunoblotting in children with atopic dematitis and positive soy challenges.

Hans–Peter Rihs et al., J. Allerg. Clin. Immuno., vol. 104:1293–1301, 1999, IgE binding of the recombinant allergen soybean profilin (rGly m 3) is mediated by conformational epitopes.

Shoji Odani et al., Eur. J. Biochem., vol. 162:485–491, 1987, Soybean hydrophobic protein.

Robert B. Goldberg et al., Cell, vol. 56:149–160, 1989, Regulation of gene expression during plant embryogenesis.

Robert K. Bush et al., Critical Rev. in Food Science & Nuitrition, vol. 36:S119–S163, Food Allergens.

V. Colot et al., EMBO J., vol. 6(12):35559–3564, 1987, Localization of sequences in wheat endosperm protein genes which confer tissue–specific expression in tobacco.

Claire Marris et al., Plant Mol. Biol. vol. 10:359–366, 1988, The 5'flanking region of a barley B hordein gene controls tissue and developmental specific CAT expression in tobacco plant.

Woo S. Lee et al., PNAS, vol. 88:6181–6185, 1991, Maize oleosin is correctly targeted to seed oil bodies in *Brassica napus* transformed with the maize oleosin gene.

Leslie M. Hoffman et al., EMBO J., vol. 6(11):3213–3221, Synthesis and protein body deposition of maize 15–kd zein in transgenic tobacco seeds.

Thomas J.V. Higgins et al., Plant Mol. Biol. vol. 11:683–695, 1988, The sequence of a pea vicillin gene and its expression in trangenic tobacco plants.

Toni Voelker et al., EMBO J., vol. 6(12):3571–3577, 1987, Differences in expression between two seed lectin alleles obtained from normal and lectin–deficient beans are maintained in transgenic tobacco.

Leslie M. Hoffman et al., Plant Mol. Biol., vol. 11:717–729, 1988, A modified storage protein is synthesized, processed, and degraded in the seeds of transgenic plants.

Michael G. Zeece et al., Food and Ag. Immunol., vol. 11:83–90, 1999, Identification of an IgE–binding region in soybean acidic glycinin G1.

Takaharu Negoro et al., Nucl. Acid Res., vol. 13(18):6719–6731, 1985, A cDNA clone encoding a glycin A1a subunit precursor of soybean.

Tadashi Ogawa et al., J. Nutr. Sci. Vitaminol., vol. 37:555–565, 1991, Investigation of the IgE–binding proteins in sobyeans by immunoblotting with the sera of the soybean–sensitive patients with atopic dermatitis.

Jack K. Okamuro et al., PNAS, vol. 83:8240–8244, 1986, Soybean seed lectin gene and flanking nonseed protein genes are developmentally regulated in transformed tobacco plants.

R. W. Yaklich et al., Crop. Sci., vol. 39:1444–1447, 1999, Analysis of the distribution of the major soybean seed allergens in a core collection of glycine max accessions.

Rudolf Valenta et al., Science, vol. 253:557–560, 1991, Identification of profilin as a novel pollen allergen; IgE autoreactivity in sensitized individuals.

Vu Huu Thanh et al., J. Agr. Food Chem., vol. 24(6):1117–1121, 1976, Major proteins of soybean seeds. A straightforward fractionation and their characterization.

C. Daniel Riggs et al., Plant Science, vol. 63:47–57, 1989, Utilization of luciferase fusion genes to monitor differential regulation of phytohemagglutinin and phaseolin promoters in transgenic tobacco.

Champa Sengupta–Gopalan et al., PNAS, vol. 82:3320–3324, 1985, Developmentally regulated expression of the bean beta–phaseolin gene in tobacco seed.

Edward J. Newbigin et al., Planta, vol. 180:461–470, 1990, Pea convicilin: structure and primary sequence of the protein and expression of a gene in the seeds of transgenic tobacco.

Luis Perez–Grau et al., Plant Cell, vol. 1:1095–1109, 1989, Soybean seed protein genes are regulated spatially during embryogenesis.

John J. Harada et al., Plant Cell, vol. 1:415–425, 1989, Soybean beta–conglycinin genes are clustered in several DNA regions and are regulated by transcriptional and post-transcriptional processes.

T. J. V. Higgins, Ann. Rev. Plant Physiol., vol. 35:191–221, 1984, Synthesis and regulation of major proteins in seeds.

Desmond G. Higgins et al., Cabios Comm., vol. 5(2):151153, 1989, Fast and sensitive multiple sequence alignments on a microcomputer.

Stephen F. Altschul et al., Nucl. Acids. Res., vol. 25(17):3389–3402, 1997, Gapped Blast and PSI–Blast: a new generation of protein database search programs.

Stephen F. Altschul et al., J. Mol. Biol., vol. 215:403–410, 1990, Basic local alignment search tool.

Jack K. Okamuro et al., Biochemistry of plants, vol. 15:1–82, 1989, Regulation of plant gene expression: general principles.

Roisin Turner et al., Mol. Bio., vol. 3:225–236, 1995, The potential exploitation of plant viral translational enhancers in biotechnology for increased gene expression.

Ivan L.W. Ingelbrecht et al., Plant Cell, vol. 1:671–680, 1989, Different 3'end regions strongly influence the level of gene expression in plant cells.

T. M. Klein et al., Nature, vol. 327, 70–73, 1987, High-velocity microprojectiles for delivering nucleicn acids into living cells.

Jonathan D.G. Jones et al., EMBO J., vol. 4(10):2411–2418, 1985, High level expression of introduced chimaeric genes in regenerated transformed plants.

Elionor R.P. De Almeida et al., Mol. Gen. Genet., vol. 218:78–86, 1989, Transgenic expression of two marker genes under the control of an Arabidopsis rbcS promoter: Sequences encoding the rubisco transit peptide increase expression levels.

Natasha Raikhel, Plant Phys., vol. 100:1627–1632, 1992, Nuclear targeting in plants.

Maureen J. Chrispeels, Ann. Rev. Plant Physiol., Plant Mol. Biol., vol. 42:21–53, 1991, Sorting of proteins in the secretory system.

Ricki M. Helm et al., Mutational Analysis of the IgE–Binding Epitopes of P34/Gly m Bd 30K, Journal of Allergy and Clinical Immunology, Feb. 2000, vol. 105, 378–384.

Masahiko Samoto et al., Substantially Complete Removal of Three Major Allergenic Soybean Proteins (Gly m Bd 30K, Gly m Bd 28K, and the Alpha–Subunit of Conglycinin) from Soy Protein by Using a Mutant Soybean, Tohoku 124, Bioscience, Biotechnology and Biochemistry, 1997, vol. 61, 2148–2150.

Tadashi Ogawa et al., Identification of the Soybean Allergenic Protein, Gly m Bd 30K, with the Soybean See 34–kDa Oil–body–associated Protein, Bioscience, Biotechnology and Biochemistry, 1993, vol. 57, 1030–1033.

* cited by examiner

SEQUENCE LISTING

<160> NUMBER OF SEQ ID NOS: 16

<210> SEQ ID NO 1
<211> LENGTH: 1156
<212> TYPE: DNA
<213> ORGANISM: chimeric construct

<400> SEQUENCE: 1

```
gcggccgcat gggtttcctt gtgttgcttc ttttctccct cttaggtctc tcttctagtt      60
ccagcatatc aactcatcgt tccatattgg accttgacct aaccaagttt accacacaga     120
aacaggtgtc ttcactgttc caactatgga agagtgagca tggacgtgtc taccataacc     180
acgaagaaga ggcaaagaga cttgagattt tcaagaataa ctcgaactat atcagggaca     240
tgaatgcaaa cagaaaatca ccccattctc atcgtttagg attgaacaag tttgctgaca     300
tcactcctca agagttcagc aaaaagtact tgcaagctcc caaggatgtg tcgcagcaaa     360
tcaaaatggc caacaagaaa atgaagaagg aacaatattc ttgtgaccat ccacctgcat     420
catgggattg gaggaaaaaa ggtgtcatca cccaagtaaa gtaccaaggg ggctgtggaa     480
ggggttgggc gttttctgcc acgggagcca tagaagcagc acatgcaata gcaacaggag     540
accttgttag cctttctgaa caagaactcg tagactgtgt ggaagaaagc gaaggttctt     600
acaatggatg gcagtatcaa tcgttcgaat gggtttttaga acatggtggc attgccactg     660
atgatgatta tccttacaga gctaaagagg gtagatgcaa agccaataag atacaagaca     720
aggttacaat tgacggatat gaaactctaa taatgtcaga tgagagtaca gaatcagaga     780
cagagcaagc gttcttaagc gccatccttg agcaaccaat tagtgtctca attgatgcaa     840
aagattttca tttatacacc gggggaattt atgatggaga aaactgtaca agtccgtatg     900
ggattaatca ctttgtttta cttgtgggtt atggttcagc ggatggtgta gattactgga     960
tagcgaaaaa ttcatgggga gaagattggg gagaagatgg ttacatttgg atccaaagaa    1020
acacgggtaa tttattagga gtgtgtggga tgaattattt cgcttcatac ccaaccaaag    1080
aggaatcaga aacactggtg tctgctcgcg ttaaaggtca tcgaagagtt gatcactctc    1140
ctctttgagc ggccgc                                                    1156
```

<210> SEQ ID NO 2
<211> LENGTH: 2970
<212> TYPE: DNA
<213> ORGANISM: chimeric construct

<400> SEQUENCE: 2

```
aagcttgatc catgcccttc atttgccgct attaattaat ttggtaacag tagtccgtac      60
```

-continued

```
taatcagtta cttatccttc ctccatcata attaatcttg gtagtctcga atgccacaac    120
actgactagt ctcttggatc ataagaaaaa gccaaggaac aaaagaagac aaaacacaat    180
gagagtatcc tttgcatagc aatgtctaag ttcataaaat tcaaacaaaa acgcaatcac    240
acacagtgga catcacttat ccactagctg aatcaggatc gccgcgtcaa gaaaaaaaaa    300
ctggacccca aaagccatgc acaacaacac gtactcacaa aggtgtcaat cgagcagccc    360
aaaacattca ccaactcaac ccatcatgag ccctcacatt tgttgtttct aacccaacct    420
caaactcgta ttctcttccg ccacctcatt tttgtttatt tcaacacccg tcaaactgca    480
tgccaccccg tggccaaatg tccatgcatg ttaacaagac ctatgactat aaatatctgc    540
aatctcggcc caggttttca tcatcaagaa ccagttcaat atcctagtac accgtattaa    600
agaatttaag atatactaac agcggccgca tgggtttcct tgtgttgctt cttttctccc    660
tcttaggtct ctcttctagt tccagcatat caactcatcg ttccatattg gaccttgacc    720
taaccaagtt taccacacag aaacaggtgt cttcactgtt ccaactatgg aagagtgagc    780
atggacgtgt ctaccataac cacgaagaag aggcaaagag acttgagatt ttcaagaata    840
actcgaacta tatcagggac atgaatgcaa acagaaaatc accccattct catcgtttag    900
gattgaacaa gtttgctgac atcactcctc aagagttcag caaaaagtac ttgcaagctc    960
ccaaggatgt gtcgcagcaa atcaaaatgg ccaacaagaa aatgaagaag gaacaatatt   1020
cttgtgacca tccacctgca tcatgggatt ggaggaaaaa aggtgtcatc acccaagtaa   1080
agtaccaagg gggctgtgga aggggttggg cgttttctgc cacggagcc atagaagcag    1140 cacatgcaat agcaacagga gaccttgtta gcctttctga acaagaactc gtagactgtg   1200
tggaagaaag cgaaggttct tacaatggat ggcagtatca atcgttcgaa tgggttttag   1260
aacatggtgg cattgccact gatgatgatt atccttacag agctaaagag ggtagatgca   1320
aagccaataa gatacaagac aaggttacaa ttgacggata tgaaactcta ataatgtcag   1380
atgagagtac agaatcagag acagagcaag cgttcttaag cgccatcctt gagcaaccaa   1440
ttagtgtctc aattgatgca aaagattttc atttatacac cggggaatt tatgatggag    1500 aaaactgtac aagtccgtat gggattaatc actttgtttt acttgtgggt tatggttcag   1560
cggatggtgt agattactgg atagcgaaaa attcatgggg agaagattgg ggagaagatg   1620
gttacatttg gatccaaaga aacacgggta atttattagg agtgtgtggg atgaattatt   1680
tcgcttcata cccaaccaaa gaggaatcag aaacactggt gtctgctcgc gttaaaggtc   1740
atcgaagagt tgatcactct cctctttgag cggccgctac atggccacgt gcatgaagta   1800
tgaactaaaa tgcatgtagg tgtaagagct catggagagc atggaatatt gtatccgacc   1860
atgtaacagt ataataactg agctccatct cacttcttct atgaataaac aaaggatgtt   1920
atgatatatt aacactctat ctatgcacct tattgttcta tgataaattt cctcttatta   1980
ttataaatca tctgaatcgt gacggcttat ggaatgcttc aaatagtaca aaaacaaatg   2040
tgtactataa gactttctaa acaattctaa ctttagcatt gtgaacgaga cataagtgtt   2100
aagaagacat aacaattata atggaagaag tttgtctcca tttatatatt atatattacc   2160
cacttatgta ttatattagg atgttaagga gacataacaa ttataaagag agaagtttgt   2220
atccatttat atattatata ctacccattt atatattata cttatccact tatttaatgt   2280
ctttataagg tttgatccat gatattcta atattttagt tgatatgtat atgaaagggt   2340
actatttgaa ctctcttact ctgtataaag gttggatcat ccttaaagtg ggtctattta   2400
```

-continued

```
attttattgc ttcttacaga taaaaaaaaa attatgagtt ggtttgataa aatattgaag    2460
gatttaaaat aataataaat aataaataac atataatata tgtatataaa tttattataa    2520
tataacattt atctataaaa aagtaaatat tgtcataaat ctatacaatc gtttagcctt    2580
gctggacgac tctcaattat ttaaacgaga gtaaacatat ttgactttt ggttatttaa     2640 caaattatta tttaacacta tatgaaattt ttttttttta tcagcaaaga aataaaatta    2700
aattaagaag gacaatggtg tgtcccaatc cttatacaac caacttccac aagaaagtca    2760
agtcagagac aacaaaaaaa caagcaaagg aaatttttta atttgagttg tcttgtttgc    2820
tgcataattt atgcagtaaa acactacaca taacccttt agcagtagag caatggttga     2880
ccgtgtgctt agcttctttt attttatttt tttatcagca aagaataaat aaaataaaat    2940
gagacacttc agggatgttt caacaagctt                                     2970
```

<210> SEQ ID NO 3
<211> LENGTH: 1600
<212> TYPE: DNA
<213> ORGANISM: Glycine max

<400> SEQUENCE: 3

```
ggggaaacaa aactaccctt ttgcttttgc tctttgttct ttgtcatgga gtggccacaa      60
caacaatggc cttccgtgat gatgagggtg gtgataaaaa gtcaccaaaa agtttgtttt     120
tgatgagcaa ctccacgagg gttttcaaga ctgatgcagg ggaaatgcgt gtgctgaaaa     180
gccatggtgg taggatattt tataggcaca tgcacattgg cttcatctct atggaaccaa    240
agtccttgtt tgttcctcag tacctcgact ccaatctcat catattcatc cgtagagggg    300
aagcaaagct gggattcata tatgatgatg aactagcgga aaggagattg aagacagggg    360
acttgtacat gattccatct ggttcagcat tctatttggt gaacatagga gaaggtcaga    420
gacttcacgt tatctgcagc attgacccct ctacaagctt gggattagag accttccagt    480
ccttctatat tggggagga gccaattcgc actcggtgct ttctggattc gaacctgcca     540
tccttgaaac tgcatttaat gaatcaagaa cggtggtaga ggaaatcttc tccaaggaac    600
tagatgggcc aattatgttc gtggatgatt ctcatgcacc tagcttatgg actaaattcc    660
ttcaactgaa gaaggatgac aaagagcaac agctgaagaa aatgatgcaa gaccaagagg    720
aggatgagga ggagaagcaa acaagtaggt catggaggaa gctcttggaa accgtatttg    780
ggaaggtgaa tgagaagata gagaacaaag acactgctgg ttcccctgcc tcttacaacc    840
tctacgatga caaaaaagcc gatttcaaaa acgcttatgt tggagcaag gcactgcatg      900 gaggcgagta tcctccactc agcgaaccgg atattggagt tttacttgtc aaactctcag    960
cgggatccat gttggcacct catgtgaatc caatatcaga tgagtatacc atagtgctga    1020
gtggttatgg tgaactgcat ataggggtatc caaacggaag caaagcaatg aaaactaaaa    1080
tcaaacaagg ggacgtgttt gttgtgccaa gatacttccc cttctgtcaa gtagcatcaa    1140
gggatggacc cttagagttc tttggcttct ccacttctgc aaggaagaac aagccacagt    1200
ttctggctgg tgctgcgtcc cttctaagga ccttgatggg gccggagctt tcggcggcgt    1260
tcggagtgag cgaggacacg ttgcggcgcg ctgttgatgc tcagcatgag gctgtgatac    1320
tgccatcagc atgggctgca ccaccggaaa atgcagggaa gctgaagatg gaagaagagc    1380
caaatgctat tagaagcttt gccaatgatg tggttatgga tgttttttaa tttgaacact    1440
tgatttggaa taggggttat ttggtagtgc tagtgcctag tggaattctg tgttgagttt    1500
tttgttcttt atatttagtt gagatgtgtg ttgtgttctt gagttgtgaa taaaaatcta    1560
```
ctttctttgt gcarraaaaa aaaaaaaaaa aaaaaaaaa         1600

<210> SEQ ID NO 4
<211> LENGTH: 454
<212> TYPE: PRT
<213> ORGANISM: Glycine max

<400> SEQUENCE: 4

```
Met Ala Phe Arg Asp Asp Glu Gly Gly Asp Lys Lys Ser Pro Lys Ser
 1               5                  10                  15

Leu Phe Leu Met Ser Asn Ser Thr Arg Val Phe Lys Thr Asp Ala Gly
             20                  25                  30

Glu Met Arg Val Leu Lys Ser His Gly Gly Arg Ile Phe Tyr Arg His
         35                  40                  45

Met His Ile Gly Phe Ile Ser Met Glu Pro Lys Ser Leu Phe Val Pro
     50                  55                  60

Gln Tyr Leu Asp Ser Asn Leu Ile Ile Phe Ile Arg Arg Gly Glu Ala
 65                  70                  75                  80

Lys Leu Gly Phe Ile Tyr Asp Asp Glu Leu Ala Glu Arg Arg Leu Lys
                 85                  90                  95

Thr Gly Asp Leu Tyr Met Ile Pro Ser Gly Ser Ala Phe Tyr Leu Val
            100                 105                 110

Asn Ile Gly Glu Gly Gln Arg Leu His Val Ile Cys Ser Ile Asp Pro
        115                 120                 125

Ser Thr Ser Leu Gly Leu Glu Thr Phe Gln Ser Phe Tyr Ile Gly Gly
    130                 135                 140

Gly Ala Asn Ser His Ser Val Leu Ser Gly Phe Glu Pro Ala Ile Leu
145                 150                 155                 160

Glu Thr Ala Phe Asn Glu Ser Arg Thr Val Val Glu Ile Phe Ser
                165                 170                 175

Lys Glu Leu Asp Gly Pro Ile Met Phe Val Asp Ser His Ala Pro
            180                 185                 190

Ser Leu Trp Thr Lys Phe Leu Gln Leu Lys Lys Asp Asp Lys Glu Gln
        195                 200                 205

Gln Leu Lys Lys Met Met Gln Asp Gln Glu Glu Asp Glu Glu Glu Lys
    210                 215                 220

Gln Thr Ser Arg Ser Trp Arg Lys Leu Leu Glu Thr Val Phe Gly Lys
225                 230                 235                 240

Val Asn Glu Lys Ile Glu Asn Lys Asp Thr Ala Gly Ser Pro Ala Ser
                245                 250                 255

Tyr Asn Leu Tyr Asp Asp Lys Lys Ala Asp Phe Lys Asn Ala Tyr Gly
            260                 265                 270

Trp Ser Lys Ala Leu His Gly Gly Glu Tyr Pro Pro Leu Ser Glu Pro
        275                 280                 285

Asp Ile Gly Val Leu Leu Val Lys Leu Ser Ala Gly Ser Met Leu Ala
    290                 295                 300

Pro His Val Asn Pro Ile Ser Asp Glu Tyr Thr Ile Val Leu Ser Gly
305                 310                 315                 320

Tyr Gly Glu Leu His Ile Gly Tyr Pro Asn Gly Ser Lys Ala Met Lys
                325                 330                 335

Thr Lys Ile Lys Gln Gly Asp Val Phe Val Pro Arg Tyr Phe Pro
            340                 345                 350

Phe Cys Gln Val Ala Ser Arg Asp Gly Pro Leu Glu Phe Phe Gly Phe
        355                 360                 365
```

```
Ser Thr Ser Ala Arg Lys Asn Lys Pro Gln Phe Leu Ala Gly Ala Ala
    370                 375                 380

Ser Leu Leu Arg Thr Leu Met Gly Pro Glu Leu Ser Ala Ala Phe Gly
385                 390                 395                 400

Val Ser Glu Asp Thr Leu Arg Arg Ala Val Asp Ala Gln His Glu Ala
                405                 410                 415

Val Ile Leu Pro Ser Ala Trp Ala Ala Pro Glu Asn Ala Gly Lys
            420                 425                 430

Leu Lys Met Glu Glu Pro Asn Ala Ile Arg Ser Phe Ala Asn Asp
        435                 440                 445

Val Val Met Asp Val Phe
    450

<210> SEQ ID NO 5
<211> LENGTH: 494
<212> TYPE: DNA
<213> ORGANISM: Glycine max
<220> FEATURE:
<221> NAME/KEY: unsure
<222> LOCATION: (9)
<223> OTHER INFORMATION: n = A, C, G, or T
<221> NAME/KEY: unsure
<222> LOCATION: (388)
<223> OTHER INFORMATION: n = A, C, G, or T
<221> NAME/KEY: unsure
<222> LOCATION: (392)..(393)
<223> OTHER INFORMATION: n = A, C, G, or T
<221> NAME/KEY: unsure
<222> LOCATION: (460)
<223> OTHER INFORMATION: n = A, C, G, or T
<221> NAME/KEY: unsure
<222> LOCATION: (463)
<223> OTHER INFORMATION: n = A, C, G, or T
<221> NAME/KEY: unsure
<222> LOCATION: (468)
<223> OTHER INFORMATION: n = A, C, G, or T

<400> SEQUENCE: 5
acacagctng cacatattac atacacgtga atcactaatt aagccatgga gaagaaatca    60
atagctgggt tgtgcttcct cttccttgtt ctctttgttg ctcaagaagt tgtggtgcaa   120
actgaggcaa agacttgcga gaacctggct gatacataca gggtccatg cttcaccact    180 ggcagctgcg atgatcactg caagaacaaa gagcacttgc tcagaggcag atgcagggac   240
gattttcgct gttggtgcac caaaaactgt taaatggatc cattcactcc aacgtgaaga   300
agatgcatgc agcgctattt tataaaaaat acaactacta tatactatat ataataagac   360
tgggcgctgc atcaatgacc ctatgtanta tnntatatat tattaccgat gtcaagaact   420
atagatgcat gtactgtgca taacggctga gttatgtccn tangttanga ataaaaataa   480
agtgctgttg ttgc                                                    494

<210> SEQ ID NO 6
<211> LENGTH: 75
<212> TYPE: PRT
<213> ORGANISM: Glycine max

<400> SEQUENCE: 6

Met Glu Lys Lys Ser Ile Ala Gly Leu Cys Phe Leu Phe Leu Val Leu
  1               5                  10                  15

Phe Val Ala Gln Glu Val Val Val Gln Thr Glu Ala Lys Thr Cys Glu
                 20                  25                  30

Asn Leu Ala Asp Thr Tyr Arg Gly Pro Cys Phe Thr Thr Gly Ser Cys
```

```
                35                  40                  45
Asp Asp His Cys Lys Asn Lys Glu His Leu Leu Arg Gly Arg Cys Arg
         50                  55                  60

Asp Asp Phe Arg Cys Trp Cys Thr Lys Asn Cys
 65                  70                  75

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: P34 gene
      primer

<400> SEQUENCE: 7
gaattcgcgg ccgcatgggt ttccttgtgt                                      30

<210> SEQ ID NO 8
<211> LENGTH: 30
<212> TYPE: DNA
<213> ORGANISM: Glycine max
<220> FEATURE:
<223> OTHER INFORMATION: Description of Artificial Sequence: P34 gene
      primer

<400> SEQUENCE: 8
gaattcgcgg ccgctcaaag aggagagtga                                      30

<210> SEQ ID NO 9
<211> LENGTH: 701
<212> TYPE: DNA
<213> ORGANISM: Glycine max

<400> SEQUENCE: 9
ttaagctttc aagagacaaa ctgctttgaa aaatgggatc caaggttgtt gcatccgttg     60
cccttctcct ctccatcaac attcttttca tttccatggt tagctccagc agccactacg    120
atccacagcc caaccttct cacgtcactg ctcttattac acgacctagt tgtccggatc     180
tgagtatttg cctcaatatt ttaggcgggt ctctaggaac cgtggatgat gttgtgccc     240 tcatcggtgg tcttggtgac attgaagcca ttgtgtgcct ttgcatccaa ctcagggccc    300
tcggaatatt aaaccttaac cgtaatttgc agttaatatt aaactcctgt ggacgaagct    360
acccgtcaaa cgccacttgc ccccgaacct aagaacagaa tatgtatggc actaattacc    420
atattacttc gtatcatggt gtttgtttgt ttgtctgtgt ttaaagttaa ggatgttata    480
cccttcgtgc ctgctacata tatatagtgg gcactataat attaccaata aattaacgtc    540
catatataag aataataata aataaataaa tatttctata caaataaagg ttacgtaatg    600
ttgttgttct cgtggatggg gatcttatct tcctcctcgc tatctttgtt tatcgtattt    660
cagtgaaagt tgttcaataa aagtcctttg ttcaacaagt g                        701

<210> SEQ ID NO 10
<211> LENGTH: 119
<212> TYPE: PRT
<213> ORGANISM: Glycine max

<400> SEQUENCE: 10

Met Gly Ser Lys Val Val Ala Ser Val Ala Leu Leu Leu Ser Ile Asn
 1               5                  10                  15

Ile Leu Phe Ile Ser Met Val Ser Ser Ser His Tyr Asp Pro Gln
             20                  25                  30
```

-continued

```
Pro Gln Pro Ser His Val Thr Ala Leu Ile Thr Arg Pro Ser Cys Pro
         35                  40                  45

Asp Leu Ser Ile Cys Leu Asn Ile Leu Gly Gly Ser Leu Gly Thr Val
 50                  55                  60

Asp Asp Cys Cys Ala Leu Ile Gly Gly Leu Gly Asp Ile Glu Ala Ile
 65                  70                  75                  80

Val Cys Leu Cys Ile Gln Leu Arg Ala Leu Gly Ile Leu Asn Leu Asn
                 85                  90                  95

Arg Asn Leu Gln Leu Ile Leu Asn Ser Cys Gly Arg Ser Tyr Pro Ser
            100                 105                 110

Asn Ala Thr Cys Pro Arg Thr
            115
```

<210> SEQ ID NO 11
<211> LENGTH: 396
<212> TYPE: DNA
<213> ORGANISM: Glycine max

<400> SEQUENCE: 11

```
atgtcgtggc aagcttatgt cgacgatcac cttctgtgtg gcatcgaagg taaccacctc     60
actcacgctg ctatcatcgg ccaagacggc agcgtttggc ttcagagtac cgacttccct    120
cagttcaaac ctgaggagat aactgccatc atgaatgact taatgagcc tggatcactt    180
gctccaactg gattgtatct cggtggcacc aaatatatgg tcatccaggg tgaacccggt    240
gctgtcattc gagggaagaa gggtcctggt ggtgttactg tgaagaagac cggtgcggcc    300
ttgatcattg gcatttatga tgaaccaatg actccaggtc aatgcaacat ggtagttgaa    360
aggcttggtg attacctcat agatcaaggc tactga                              396
```

<210> SEQ ID NO 12
<211> LENGTH: 131
<212> TYPE: PRT
<213> ORGANISM: Glycine max

<400> SEQUENCE: 12

```
Met Ser Trp Gln Ala Tyr Val Asp Asp His Leu Leu Cys Gly Ile Glu
 1               5                  10                  15

Gly Asn His Leu Thr His Ala Ala Ile Ile Gly Gln Asp Gly Ser Val
             20                  25                  30

Trp Leu Gln Ser Thr Asp Phe Pro Gln Phe Lys Pro Glu Glu Ile Thr
         35                  40                  45

Ala Ile Met Asn Asp Phe Asn Glu Pro Gly Ser Leu Ala Pro Thr Gly
 50                  55                  60

Leu Tyr Leu Gly Gly Thr Lys Tyr Met Val Ile Gln Gly Glu Pro Gly
 65                  70                  75                  80

Ala Val Ile Arg Gly Lys Lys Gly Pro Gly Gly Val Thr Val Lys Lys
                 85                  90                  95

Thr Gly Ala Ala Leu Ile Ile Gly Ile Tyr Asp Glu Pro Met Thr Pro
            100                 105                 110

Gly Gln Cys Asn Met Val Val Glu Arg Leu Gly Asp Tyr Leu Ile Asp
            115                 120                 125

Gln Gly Tyr
       130
```

<210> SEQ ID NO 13
<211> LENGTH: 396

<210> SEQ ID NO 13
<211> LENGTH: (not shown)
<212> TYPE: DNA
<213> ORGANISM: Glycine max

<400> SEQUENCE: 13

```
atgtcctggc aggcgtatgt cgacgatcac cttctgtgtg acatcgaagg taaccacctc      60
actcacgctg ctatcatcgg ccaagacggc agcgtttggg ctcagagtac cgacttccct     120
cagttcaaac ctgaggagat aactgccatc atgaatgact taatgagccc tggatcactt     180
gctccaactg gattgtatct cggtggcacc aaatatatgg tcatccaggg tgaacccggt     240
gctgtcattc gagggaagaa gggtcctggt ggtgttactg tgaagaagac cggtgcggcc     300
ttgatcattg gcatttatga tgaaccaatg actccaggtc aatgcaacat ggtagttgaa     360
aggcctggtg attacctcat cgaccagggc tactga                               396
```

<210> SEQ ID NO 14
<211> LENGTH: 131
<212> TYPE: PRT
<213> ORGANISM: Glycine max

<400> SEQUENCE: 14

```
Met Ser Trp Gln Ala Tyr Val Asp Asp His Leu Leu Cys Asp Ile Glu
  1               5                  10                  15

Gly Asn His Leu Thr His Ala Ala Ile Ile Gly Gln Asp Gly Ser Val
             20                  25                  30

Trp Ala Gln Ser Thr Asp Phe Pro Gln Phe Lys Pro Glu Glu Ile Thr
         35                  40                  45

Ala Ile Met Asn Asp Phe Asn Glu Pro Gly Ser Leu Ala Pro Thr Gly
     50                  55                  60

Leu Tyr Leu Gly Gly Thr Lys Tyr Met Val Ile Gln Gly Glu Pro Gly
 65                  70                  75                  80

Ala Val Ile Arg Gly Lys Lys Gly Pro Gly Gly Val Thr Val Lys Lys
                 85                  90                  95

Thr Gly Ala Ala Leu Ile Ile Gly Ile Tyr Asp Glu Pro Met Thr Pro
            100                 105                 110

Gly Gln Cys Asn Met Val Val Glu Arg Pro Gly Asp Tyr Leu Ile Asp
        115                 120                 125

Gln Gly Tyr
    130
```

<210> SEQ ID NO 15
<211> LENGTH: 1746
<212> TYPE: DNA
<213> ORGANISM: Glycine max

<400> SEQUENCE: 15

```
aaaacaactc aaacattctc tccattggtc cttaaacact catcagtcat caccatggcc      60
aagctagttt tttcccttg ttttctgctt tcagtggct gctgcttcgc tttcagttcc      120
agagagcagc ctcagcaaaa cgagtgccag atccaaaaac tcaatgccct caaaccgggt     180
aaccgtatag agtcagaagg agggctcatt gagacatgga accctaacaa caagccattc     240
cagtgtgccg tgttgccct ctctcgctgc accctcaacc gcaacgccct tcgtagacct     300
tcctacacca acggtcccca agaaatctac atccaacaag gtaagggtat ttttggcatg     360
atatacccgg ttgttctag cacatttgaa gagcctcaac aacctcaaca aagaggacaa     420
agcagcagac cacaagaccg tcaccagaag atctataact ccagagaggg tgatttgatc     480
gcagtgccta ctggtgttgc atggtggatg tacaacaatg aagacactcc tgttgttgcc     540
```

```
gtttctatta ttgacaccaa cagcttggag aaccagctcg accagatgcc taggagattc      600
tatcttgctg ggaaccaaga gcaagagttt ctaaaatatc agcaagagca aggaggtcat      660
caaagccaga aaggaaagca tcagcaagaa gaagaaaacg aaggaggcag catattgagt      720
ggcttcaccc tggaattctt ggaacatgca ttcagcgtgg acaagcagat agcgaaaaac      780
ctacaaggag agaacgaagg ggaagacaag ggagccattg tgacagtgaa aggaggtctg      840
agcgtgataa aaccacccac ggacgagcag caacaaagac cccaggaaga ggaagaagaa      900
gaagaggatg agaagccaca gtgcaagggt aaagacaaac actgccaacg cccccgagga      960
agccaaagca aaagcagaag aaatggcatt gacgagacca tatgcaccat gagacttcgc     1020
cacaacattg ccagacttc atcacctgac atctacaacc tcaagccgg tagcgtcaca      1080 accgccacca gccttgactt cccagccctc tcgtggctca gactcagtgc tggatttggg     1140
tctctccgca agaatgcaat gttcgtgcca cactacaacc tgaacgcgaa cagcataata     1200
tacgcattga atggacgggc attgatacaa gtggtgaatt gcaacggtga gagtgtttt     1260 gatggagagc tgcaagaggg acgggtgctg atcgtgccac aaaactttgt ggtggctgca     1320
agatcacaga gtgacaactt cgagtatgtg tcattcaaga ccaatgatac acccatgatc     1380
ggcactcttg cagggcaaa ctcattgttg aacgcattac agaggaagt gattcagcac      1440 actttcaacc taaaaagcca gcaggccagg cagataaaga caacaacccc tttcaagttc     1500
ctggttccac ctcaggagtc tcagaagaga gctgtggctt agagcccttt ttgtatgtgc     1560 tacccccactt ttgtcttttt ggcaatagtg ctagcaacca ataaataata ataataataa     1620
tgaataagaa aacaaaggct ttagcttgcc ttttgttcac tgtaaaataa taatgtaagt     1680
actctctata atgagtcacg aaacttttgc gggaataaaa ggagaaattc caatgagttt     1740
tctgtt                                                                 1746
```

<210> SEQ ID NO 16
<211> LENGTH: 495
<212> TYPE: PRT
<213> ORGANISM: Glycine max

<400> SEQUENCE: 16

```
Met Ala Lys Leu Val Phe Ser Leu Cys Phe Leu Leu Phe Ser Gly Cys
  1               5                  10                  15

Cys Phe Ala Phe Ser Ser Arg Glu Gln Pro Gln Gln Asn Glu Cys Gln
             20                  25                  30

Ile Gln Lys Leu Asn Ala Leu Lys Pro Gly Asn Arg Ile Glu Ser Glu
         35                  40                  45

Gly Gly Leu Ile Glu Thr Trp Asn Pro Asn Asn Lys Pro Phe Gln Cys
     50                  55                  60

Ala Gly Val Ala Leu Ser Arg Cys Thr Leu Asn Arg Asn Ala Leu Arg
 65                  70                  75                  80

Arg Pro Ser Tyr Thr Asn Gly Pro Gln Glu Ile Tyr Ile Gln Gln Gly
                 85                  90                  95

Lys Gly Ile Phe Gly Met Ile Tyr Pro Gly Cys Ser Ser Thr Phe Glu
            100                 105                 110

Glu Pro Gln Gln Pro Gln Gln Arg Gly Gln Ser Ser Arg Pro Gln Asp
        115                 120                 125
```

-continued

```
Arg His Gln Lys Ile Tyr Asn Ser Arg Glu Gly Asp Leu Ile Ala Val
    130                 135                 140
Pro Thr Gly Val Ala Trp Trp Met Tyr Asn Asn Glu Asp Thr Pro Val
145                 150                 155                 160
Val Ala Val Ser Ile Ile Asp Thr Asn Ser Leu Glu Asn Gln Leu Asp
                165                 170                 175
Gln Met Pro Arg Arg Phe Tyr Leu Ala Gly Asn Gln Glu Gln Glu Phe
            180                 185                 190
Leu Lys Tyr Gln Gln Glu Gln Gly His Gln Ser Gln Lys Gly Lys
        195                 200                 205
His Gln Gln Glu Glu Glu Asn Glu Gly Gly Ser Ile Leu Ser Gly Phe
    210                 215                 220
Thr Leu Glu Phe Leu Glu His Ala Phe Ser Val Asp Lys Gln Ile Ala
225                 230                 235                 240
Lys Asn Leu Gln Gly Glu Asn Glu Gly Glu Asp Lys Gly Ala Ile Val
                245                 250                 255
Thr Val Lys Gly Gly Leu Ser Val Ile Lys Pro Pro Thr Asp Glu Gln
            260                 265                 270
Gln Gln Arg Pro Gln Glu Glu Glu Glu Glu Asp Glu Lys Pro
        275                 280                 285
Gln Cys Lys Gly Lys Asp Lys His Cys Gln Arg Pro Arg Gly Ser Gln
    290                 295                 300
Ser Lys Ser Arg Arg Asn Gly Ile Asp Glu Thr Ile Cys Thr Met Arg
305                 310                 315                 320
Leu Arg His Asn Ile Gly Gln Thr Ser Ser Pro Asp Ile Tyr Asn Pro
                325                 330                 335
Gln Ala Gly Ser Val Thr Thr Ala Thr Ser Leu Asp Phe Pro Ala Leu
            340                 345                 350
Ser Trp Leu Arg Leu Ser Ala Gly Phe Gly Ser Leu Arg Lys Asn Ala
        355                 360                 365
Met Phe Val Pro His Tyr Asn Leu Asn Ala Asn Ser Ile Ile Tyr Ala
    370                 375                 380
Leu Asn Gly Arg Ala Leu Ile Gln Val Val Asn Cys Asn Gly Glu Arg
385                 390                 395                 400
Val Phe Asp Gly Glu Leu Gln Glu Gly Arg Val Leu Ile Val Pro Gln
                405                 410                 415
Asn Phe Val Val Ala Ala Arg Ser Gln Ser Asp Asn Phe Glu Tyr Val
            420                 425                 430
Ser Phe Lys Thr Asn Asp Thr Pro Met Ile Gly Thr Leu Ala Gly Ala
        435                 440                 445
Asn Ser Leu Leu Asn Ala Leu Pro Glu Glu Val Ile Gln His Thr Phe
    450                 455                 460
Asn Leu Lys Ser Gln Gln Ala Arg Gln Ile Lys Asn Asn Pro Phe
465                 470                 475                 480
Lys Phe Leu Val Pro Pro Gln Glu Ser Gln Lys Arg Ala Val Ala
                485                 490                 495
```

US 6,864,362 B2

HYPOALLERGENIC TRANSGENIC SOYBEANS

This application claims the benefit under 35 U.S.C. § 119(e) of U.S. Provisional Application 60/189,823, filed Mar. 16, 2000.

FIELD OF THE INVENTION

This invention relates to hypoallergenic transgenic soybeans and, in particular, to the preparation of recombinant expression constructs to lower soybean vacuolar protein, commonly know as P34, as well as other allergens such as Gly m IA, Gly m IB, rGLY m3 and Glycinin G1 (AlaB1b). Such constructs can be used to produce hypoallergenic transgenic soybean plants that in turn can be used to make hypoallergenic soybean products which can be used in a variety of food and feed applications.

BACKGROUND OF THE INVENTION

Food allergy is a serious nutritional problem in children and adults. Basically, any food that contains protein has the potential to elicit an allergic reaction in a percentage of the human population. Most food-allergic reactions are attributable to cows' milk, eggs, fish, crustaceans, peanuts, soybeans, tree nuts and wheat. Sometimes referred to as "the Big Eight", it is estimated that these foods or food groups account for more than 90% of all food allergies in the United States. (Taylor et al., (1999) *Nutrition Today* 34:15–22).

The allergens in foods are almost always naturally occurring proteins. Although foods contain millions of individual proteins, only a comparative few food proteins have been documented as being allergens. Some foods are known to contain multiple allergenic proteins, including soybeans, peanuts, cows' milk and eggs. (Burks et al., (1988) *J. Allergy Clin. Immunol.* 81:1135–42; Thanh et al., (1976) *J. Agr. Food Chem.* 24:1117–21).

Improved isolation techniques resulting in better flavor and increased functionality has resulted in widespread use of soy protein isolates and concentrates in a variety of food products in amounts that could trigger an allergic reaction in soybean-sensitive individuals. Soybean protein allergies pose a significant problem for large numbers of people because soybean protein is now a common constituent of many processed foods. For sensitive individuals, avoiding soybean products is difficult and poses significant limitations in choosing processed and convenience foods. Since the incidence of soybean-related food allergies is increasing in many countries including the U.S. (Taylor et al., Chemistry of Food Allergens in Food Allergy, Chandra R. K. (ed.): Food Allergy, Nutrition Research Education Foundation, 1987, pp 21–44), there is an ever-growing need to develop hypoallergenic soybean products to address this issue.

The major human allergen of soybean seeds is a protein designated Gly m Bd 30K also referred to as P34 because this protein has been shown to have an N-terminal amino acid sequence and amino acid composition identical to that of the soybean seed 34 kDa seed vacuolar protein, P34. Gly m Bd 30K was described by (Ogawa et al., (1991) *J. Nutr. Sci. Vitaminol.* 37:555–565), as a 30-kDa mol wt protein, a minor constituent of the 7S globulin fraction. Gly m Bd 30K is an outlying member of the papain-superfamily of cysteine-proteases and is present in processed food products that contain soybean protein. (Yaklich et al., (1999) *Crop Science* 39:1444). Results have indicated that it may not be possible to eliminate P34 from the food supply by breeding with an improved germplasm base. (Yaklich et al., (1999) *Crop Science* 39:1444). Thus, the elimination of P34 from soybean seeds, as well as other allergens allergens such as Gly m IA, Gly m IB, rGLY m3 and Glycinin G1 (AlaB1b), by using recombinant technology not only would enhance food safety but it would make the use of soybean products available to sensitive individuals.

SUMMARY OF THE INVENTION

This invention concerns a recombinant expression construct to lower Gly m Bd 30K (soybean vacuolar protein P34) content of a soybean which comprises a promoter operably linked to an isolated Gly m Bd 30K nucleic acid fragment corresponding substantially to the nucleotide sequence set forth in SEQ ID NO:1 or a functionally equivalent subfragment thereof.

In a second embodiment, this invention concerns a recombinant expression construct for producing a hypoallergenic soybean which comprises an isolated KSTI nucleic acid fragment corresponding substantially to the nucleotide sequence set forth in SEQ ID NO:2 or a functionally equivalent subfragment thereof operably linked to an isolated Gly m Bd 28K nucleic acid fragment corresponding substantially to the nucleotide sequence set forth in SEQ ID NO:3 or a functionally equivalent subfragment thereof.

In a third embodiment, this invention concerns a hypoallergenic soybean plant comprising in its genome at least one of the claimed recombinant expression constructs. Also of interest are seeds obtained from such plants, oil obtained from these seeds and products made from the hydrogenation, fractionation, interesterification or hydrolysis of oil obtained from the seeds of such plants.

In a fourth embodiment, this invention concerns a hypoallergenic soybean product, and any food or any feed incorporating this soybean product or oil.

In a fifth embodiment, this invention concerns a method for making a hypoallergenic soy products from hypoallergenic soybean seeds which comprises:

(a) cracking the seeds obtained from a transgenic hypoallergenic soybean plant of the invention to remove the meats from the hulls; and (b) flaking the meats obtained in step (a) to obtain the desired flake thickness.

In a sixth embodiment, this invention concerns a method for making a hypoallergenic soybean plant which comprises:

(a) crossing a first parent soybean which is a soybean plant comprising in its genome recombinant expression construct to lower the Gly m Bd 30K (soybean vacuolar protein P34) content of a soybean which comprises a beta-conglycinin promoter operably linked to an isolated Gly m Bd 30K nucleic acid fragment corresponding substantially to the nucleotide sequence set forth in SEQ ID NO:1 or a functionally equivalent subfragment thereof, with a second soybean parent which is substantially free of one or more allergens selected from the group consisting Gly m Bd 28K, alpha-subunit of beta-conglycinin, KSTI, Gly m2, Gly m IA, Gly m IB, rGLY m3 and Glycinin G1; and (b) selecting progeny plants of the cross of step (a) which are hypoallergenic.

In a seventh embodiment, this invention concerns a method for making a hypoallergenic soybean plant which comprises:

(a) crossing a first parent soybean which is a soybean plant comprising in its genome the recombinant expression construct to lower the Gly m Bd 30K (Soybean vacuolar protein P34) content of a soybean which comprises a beta-conglycinin promoter operably linked to an isolated Gly m Bd 30K nucleic acid fragment corresponding substantially to the nucleotide sequence set forth in SEQ ID NO:1 or a functionally equivalent subfragment thereof, with a second soybean parent which is naturally occurring soybean mutant which is substantially free of Gly m Bd 28K and which is substantially free of the alpha-subunit of beta-conglycinin; and (b) selecting progeny plants of the cross of step (a) which are hypoallergenic.

In an eighth embodiment, this invention concerns a method for making a hypoallergenic soybean plant which comprises:

(a) crossing a first parent soybean which is a soybean plant comprising in its genome any of the claimed recombinant constructs with a second soybean parent wherein the second parent is selected from the group consisting of a soybean plant comprising in its genome a recombinant expression construct which produces a lower level of the alpha subunit of beta-conglycinin or a naturally occuring variant therof; and (b) selecting progeny plants of the cross of step (a) which are hypoallergenic.

In a ninth embodiment, this invention concerns a method for making a hypoallergenic soybean plant which comprises:

(a) crossing a first parent soybean which is the soybean plant comprising in its genome any of the claimed recombinant constructs with a second soybean parent wherein the second parent comprises naturally occurring mutant soybean plants which are substantially free of the KSTI allergen; and (b) selecting progeny plants of the cross of step (a) which are hypoallergenic.

Also of interest are seeds obtained from plants made by these methods, oil obtained from these seeds, products made from the hydrogenation, fractionation, interesterification or hydrolysis of oil obtained from the seeds of such plants, hypoallergenic soybean products, and food, infant formula and animal feed incorporating any of the hypoallergenic soybean products or oils.

In a tenth embodiment, this invention concerns an isolated nucleic acid fragment comprising a nucleic acid sequence encoding a soybean Gly m Bd 28K protein. The protein which is encoded can have an amino acid identity of 49% or greater to the polypeptide encoded by SEQ ID NO:4 or a functionally equivalent subfragment thereof. In another aspect, this isolated nucleic acid fragment can have a nucleic acid identity of 48% or greater to the sequence set forth in SEQ ID NO:3. Also of interest is any plant Gly m Bd 28K protein having an amino acid identity of 49% or greater to the polypeptide sequence set forth in SEQ ID NO:4. Chimeric genes comprising such nucleic acid fragments or the reverse complement thereof operably to regulatory sequences are also of interest as well as hypoallergenic soybean plants comprising such chimeric genes, seeds obtained from such plants, oil obtained from such seeds, and products made from the hydrogenation, fractionation, interesterification or hydrolysis of oil obtained from the seeds of such plants. In still another aspect, this invention concerns a hypoallergenic soybean product, and any food or any feed incorporating this soybean product or oil.

In an eleventh embodiment, this invention concerns an isolated nucleic acid fragment comprising a nucleic acid sequence encoding a soybean Gly m 2 protein. The protein which is encoded can have an amino acid identity of 95% or greater to the polypeptide sequence set forth in SEQ ID NO:6 or a functionally equivalent subfragment thereof. Also of interest is any plant Gly m 2 protein having an amino acid identity of 95% or greater to the polypeptide sequence set forth in SEQ ID NO:4. Chimeric genes comprising such nucleic acid fragments or the reverse complement thereof operably to regulatory sequences are also of interest as well as hypoallergenic soybean plants comprising such chimeric genes, seeds obtained from such plants, oil obtained from such seeds, and products made from the hydrogenation, fractionation, interesterification or hydrolysis of oil obtained from the seeds of such plants. In still another aspect, this invention concerns a hypoallergenic soybean product, and any food or any feed incorporating this soybean product or oil.

In a twelfth embodiment, this invention concerns a recombinant expression construct to lower Gly m IB content of a soybean which comprises a promoter operably linked to an isolated Gly m IB nucleic acid fragment corresponding substantially to the nucleotide sequence set forth in SEQ ID NO:9 or a functionally equivalent subfragment thereof.

In a thirteenth embodiment, this invention concerns a recombinant expression construct to lower Gly m IB content of a soybean which comprises a promoter operably linked to an isolated Gly m IB nucleic acid fragment corresponding substantially to the nucleotide sequence set forth in SEQ ID NO:9 or a functionally equivalent subfragment thereof.

In a fourteenth embodiment, this invention concerns a recombinant expression construct to lower rGLY m3 content of a soybean wherein which comprises a promoter operably linked to an isolated rGly m3 nucleic acid fragment corresponding substantially to the nucleotide sequence set forth in SEQ ID NOs:11 and 13 or a functionally equivalent subfragment thereof.

In a fifteenth embodiment, this invention concerns a recombinant expression construct to lower Glycinin G1 (AlaB1b) content of a soybean wherein which comprises a promoter operably linked to an isolated Glycinin G1 nucleic acid fragment corresponding substantially to the nucleotide sequence set forth in SEQ ID NO:15 or a functionally equivalent subfragment thereof.

Also of interest are a hypoallergenic soybean plant comprising in its genome at least one of the claimed recombinant expression constructs. Also of interest are seeds obtained from such plants, oil obtained from these seeds and products made from the hydrogenation, fractionation, interesterification or hydrolysis of oil obtained from the seeds of such plants. In still another aspect, this invention concerns a hypoallergenic soybean product, and any food or any feed incorporating this soybean product or oil.

BRIEF DESCRIPTION OF THE FIGURES AND SEQUENCE DESCRIPTIONS

FIG. 1 depicts soy protein processing.

FIG. 2 shows a stained protein gel and the subsequent antibody detection of the Gly 1 m protein on the nitrocellulose filter blot. The proteins were obtained from transgenic somatic embryos that did (7-1) or did not (3-1 and 6-1) exhibit co-suppression of Gly I m. A control positive is included in the last lane of the blot.

FIG. 3 shows an SDS acrylamide gel of seed proteins taken from independent isolates of delta-12 desaturase (Fad2) co-suppressed soybean plants transformed with pKS68 (see Example 8). Note that in each lane where the α'-subunit of beta-conglycinin is reduced or missing the α-subunit is also missing (lanes 1, 3, 4, 5, 6, 7, and 9). Lanes 1 and 2 are a positive and negative control (respectively).

Figure 1:
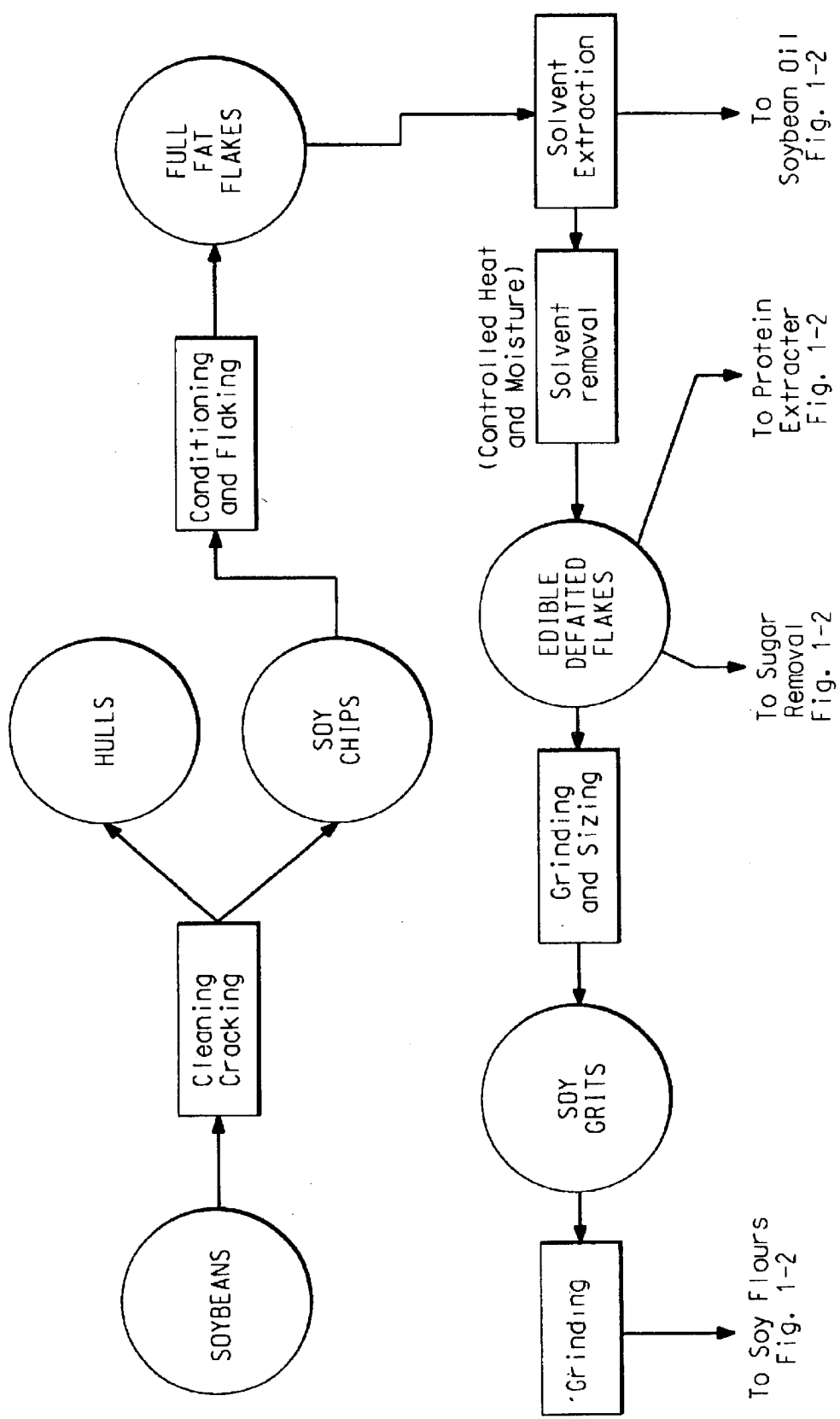

SEQ ID NO:1 is the nucleotide sequence of the cDNA insert in clone pKS73 encoding a soybean P34 protein. The sequence starts and ends with the NotI sites that were part of the primer sequences used in the construction of the insert (see Example 1). The promoter that directs the synthesis of P34 in pKS73 is from the beta-conglycinin gene, and the 3'-untranslated region is from the phaseolin gene.

SEQ ID NO:2 is the nucleotide sequence of the Kunitz soybean trypsin inhibitor (KSTI) introduced into plants to co-suppress the endogenous protein.

SEQ ID NO:3 is the nucleotide sequence portion of the cDNA insert in clone se6.pk0050.c3 encoding a substantial portion of a soybean Gly m Bd 28K protein.

SEQ ID NO:4 is the deduced amino acid sequence of a substantial portion of a soybean Gly m Bd 28K protein derived from the nucleotide sequence of SEQ ID NO:3.

SEQ ID NO:5 is the nucleotide sequence portion of the cDNA insert in clone sls1c.pk027.a11 encoding a substantial portion of a soybean Gly m2 protein.

SEQ ID NO:6 is the deduced amino acid sequence of a substantial portion of a soybean Gly m2 protein derived from the nucleotide sequence of SEQ ID NO:5.

SEQ ID NO:7 is the sequence of a synthetic oligonucleotide used to amplify the P34 coding region incorporated into the construct of SEQ ID NO:1.

SEQ ID NO:8 is the sequence of a synthetic oligonucleotide used to amplify the P34 coding region incorporated into the construct of SEQ ID NO:1.

SEQ ID NO:9 is the nucleotide sequence portion of the cDNA insert from Genbank accession number AF100160 (Odani et al. (1987) *Eur J Biochem* 162:485–491), encoding a substantial portion of a Glycine max (soybean) Gly m IA, a "hydrophobic protein from soybean". Gly m IB is identical to Gly m IA but is missing 3 amino acids from the amino terminus. Both proteins are believed to be minor human allergens.

SEQ ID NO:10 is the deduced amino acid sequence of a substantial portion of a soybean Gly m IA protein derived from the nucleotide sequence of SEQ ID NO:9.

SEQ ID NO:11 is the nucleotide sequence portion of the cDNA insert from Genbank accession number AJ223981 (Rihs et al. (1999) *J. Allergy Clin Immunol* 104: 1293–1301), encoding a substantial portion of a *Glycine max* (soybean) rGly m3, a "soybean profilin homologue". This protein binds IgE antibodies, and is tentatively identified as a soybean allergen.

SEQ ID NO:12 is the deduced amino acid sequence of a substantial portion of a soybean rGly m3 protein derived from the nucleotide sequence of SEQ ID NO:11.

SEQ ID NO:13 is the nucleotide sequence portion of the cDNA insert from Genbank accession number AJ223982 (Rihs et al. (1999) *J. Allergy Clin Immunol* 104:1293–1301), encoding a substantial portion of a Glycine max (soybean) rGly m3, a "soybean profilin homologue". This protein binds IgE antibodies, and is tentatively identified as a soybean allergen.

SEQ ID NO:14 is the deduced amino acid sequence of a substantial portion of a soybean rGly m3 protein derived from the nucleotide sequence of SEQ ID NO:13.

SEQ ID NO:15 is the nucleotide sequence portion of the cDNA insert from Genbank accession number X02985 (Zeece et al. (1999) *Food and Agric Immunol* 11:83–90), encoding a substantial portion of a Glycine max (soybean) glycinin G1 (or AlaB1b). Soybean glycinin G1 binds IgE antibodies in its acidic domain, and is tentatively identified as a soybean allergen.

SEQ ID NO:16 is the deduced amino acid sequence of a substantial portion of a soybean glycinin G 1 (or AlaB1b) protein derived from the nucleotide sequence of SEQ ID NO:15.

DETAILED DESCRIPTION OF THE INVENTION

In the context of this disclosure, a number of terms shall be utilized.

The terms "P34 (soybean vacuolar protein)" and "Gly m BD 30K" and "Gly m 1" [SEQ ID NO:1] are used interchangeably herein. They all refer to the major soybean seed allergen. Major allergens are generally defined as proteins for which 50% or more of the allergic patients studied have specific IgE.

The terms "KSTI" and "KTi3" [SEQ ID NO:2] are used interchangeably herein. They refer to a Kunitz soybean trypsin inhibitor or a Kunitz-type soybean trypsin inhibitor which is a minor soybean seed allergen. S-II is another minor soybean seed allergen along with 68-kDa which is the α-subunit of β-conglycinin.

The terms "Gly m Bd 28K" and "28K protein" [SEQ ID NOs:3 and 4] are used interchangeably herein. They refer to a 28 kilodalton protein which is a minor soybean seed allergen.

The term "Gly m2" [SEQ ID NOs:5 and 6] refers to a small 75-amino acid protein that is a minor soybean seed allergen.

The term Gly m IA [SEQ ID NOs:9 and 10] and Gly m IB refer to a hydrophobic soybean seed protein that has similarity to lipid transfer proteins. Gly m IA is a 119 amino acid protein and Gly m IB is identical except it is missing the first three amino acid residues of the polypeptide. Both are considered minor soybean seed allergens.

The term rGly M3 [SEQ ID NOs:11, 12, 13, and 14] refers to a soybean profilin-like protein of 131 amino acids that binds human IgE antibody. Plant profilins have been reported to be a pan-allergen in pollen (Valenta et al. (1991) *Science* 253:557–560).

The term glycinin G1 [SEQ ID NOs:15 and 16] refers to a 495 amino acid soybean glycinin protein. This protein contains an acid domain that binds to IgE antibody. Glycinin G2 which contains a shorter (by 20 amino acids) acidic chain does not bind IgE [Zeece et al. (1999) *Food and Agric Immunol* 11:83–90]. As noted above for the rGly m3 profilin, IgE binding proteins are thought to be potential allergens.

The term "hypoallergenic" means substantially free of any allergens, i.e., an immunological response, such as an allergic reaction, should not be triggered.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Nucleotides are referred to by their single letter designation as follows: "A" for adenosine, "C" for cytidine, "G" for guanosine, "T" for thymidine, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropriate orientation relative to a plant promoter sequence.

The terms "substantially similar" and "corresponding substantially" as used herein refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Preferred substantially similar nucleic acid sequences encompassed by this invention are those sequences that are 45% identical to the nucleic acid fragments reported herein or which are 45% identical to any portion of the nucleotide sequences reported herein. More preferred are nucleic acid fragments which are 50% identical to the nucleic acid sequences reported herein, or which are 50% identical to any portion of the nucleotide sequences reported herein. Most preferred are nucleic acid fragments which are 60% identical to the nucleic acid sequences reported herein, or which are 60% identical to any portion of the nucleotide sequences reported herein. Sequence alignments and percent similarity calculations may be determined using a variety of comparison methods designed to detect homologous sequences including, but not limited to, the Megalign program of the LASARGENE bioinformatics computing suite (DNASTAR Inc., Madison, Wis.). Multiple alignment of the sequences are performed using the Clustal method of alignment (Higgins and Sharp (1989) *CABIOS.* 5:151–153) with the default parameters (GAP PENALTY= 10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F., et al., (1993) *J. Mol. Biol.* 215:403–410) and Gapped Blast (Altschul, S. F. et al., (1997) *Nucleic Acids Res.* 25:3389–3402).

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the klenow fragment of DNA polymerase I. "Sense" RNA refers to RNA transcript that includes the mRNA and so can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the production of a functional end-product. Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

"Altered expression" refers to the production of gene product(s) in transgenic organisms in amounts or proportions that differ significantly from that activity in comparable tissue (organ and of developmental type) from wild-type organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence that is translated in conjunction with a protein and directs the protein to the secretory system (Chrispeels, J. J., (1991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100: 1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) Nature (London) 327:70–73; U.S. Pat. No. 4,945,050), or an Agrobacterium-mediated method using an appropriate Ti plasmid containing the transgene (Ishida Y. et al., 1996, Nature Biotech. 14:745–750).

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

The terms "expression construct" and "recombinant expression construct" are used interchangeably herein. These terms, as used herein, comprise any of the isolated nucleic acid fragments of the invention or subfragment thereof used either alone or in combination with each other as discussed herein. They can be incorporated into recombinant nucleic acid constructs, typically DNA constructs, capable of introduction into and replication in a host cell. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) EMBO J. 4:2411–2418; De Almeida et al., (1989) Mol. Gen. Genetics 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

As was noted above P34 constitutes the major allergen in soybeans and is present in processed food products that contain soybean protein. Assays of IgE binding using immunoglobulins from soybean sensitive individuals indicates that 65% of the total allergenic response can be attributed to P34. Detailed immunological analysis of the allergenicity of P34 by epitope mapping has shown that there are at least 12 distinct epitopes on the protein.

P34 possesses most of the conserved characteristics of cysteine proteases including a large precursor domain that is posttranslationally processed. The primary sequence contains aligned and conserved amino acids that are important in the conserved tertiary conformation of the papain superfamily. P34 exhibits some unique features that separate it from other members of the papain superfamily. Among these are replacement of the conserved cysteine in the active site found in all other papain family proteins with a glycine, suggesting that the protein is enzymatically inactive. Cysteine proteases are typically self-processed under acid-reducing conditions resulting in the cleavage of the large precursor domain. However, P34 is processed after an asparagine residue in a single step, most likely by the same enzyme that processes the 11S storage proteins. Sequence comparisons and alignments indicate that although P34 is a member of the papain superfamily, it is also quite dissimilar from the enzymatically active cysteine proteases including those identified in soybean.

P34 may have a function in defense against Pseudomonas infection by binding syringolide elicitors secreted the bacteria. P34 is very abundant in seeds, but it is also found in vegetative cells that are subject to bacterial infections.

It has been found that the P34 allergen can be substantially removed from soybean embryos, without resulting lethality to the embryo, by using recombinant techniques such as sense suppression of an isolated nucleic acid fragment encoding P34 protein.

Thus, in one embodiment, the instant invention concerns a recombinant expression construct to lower Gly m Bd 30K (Soybean vacuolar protein P34) content of a soybean which comprises a promoter operably linked to an isolated Gly m Bd 30K nucleic acid fragment corresponding substantially to the nucleotide sequence set forth in SEQ ID NO:1 or a functionally equivalent subfragment thereof. A transgenic soybean plant which comprises the foregoing recombinant expression construct in its genome should be hypoallergenic with respect to P34.

Any promoter can be used to practice the invention. There can be mentioned a beta-conglycinin promoter, a Kunitz Trypsin Inhibitor (KSTI) promoter, a Gly m Bd 28K promoter, T7 promoter, a 35S promoter and a beta-phaseolin promoter. The preferred promoter is that of the α'-subunit of beta-conglycinin (referred to herein as the beta-conglycinin promoter). Co-suppressed plants that contain recombinant expression constructs with the promoter of the α'-subunit of beta-conglycinin will often exhibit suppression of both the α and α' subunits of beta-congylcinin (as described in PCT Publication No. WO97/47731, published on Dec. 18, 1997, the disclosure of which is hereby incorporated by reference). Particularly preferred promoters are those that allow seed-specific expression. This may be especially useful since seeds are the primary source consumable protein and oil, and also since seed-specific expression will avoid any potential deleterious effect in non-seed tissues. This may be particularly important for plants with reduced or undetectable levels of p34, since no naturally occurring or induced mutations have been recovered in this gene, implying a deleterious effect for plants lacking this protein.

Examples of seed-specific promoters include, but are not limited to, the promoters of seed storage proteins, which can represent up to 90% of total seed protein in many plants. The seed storage proteins are strictly regulated, being expressed almost exclusively in seeds in a highly tissue-specific and stage-specific manner (Higgins et al., (1984) *Ann. Rev. Plant Physiol.* 35:191–221; Goldberg et al., (1989) *Cell* 56:149–160). Moreover, different seed storage proteins may be expressed at different stages of seed development.

Expression of seed-specific genes has been studied in great detail (See reviews by Goldberg et al., (1989) *Cell* 56:149–160 and Higgins et al., (1984) *Ann. Rev. Plant Physiol.* 35:191–221). There are currently numerous examples of seed-specific expression of seed storage protein genes in transgenic dicotyledonous plants. These include genes from dicotyledonous plants for bean β-phaseolin (Sengupta-Gopalan et al., (1985) *Proc. Natl. Acad. Sci. USA* 82: 3320–3324; Hoffman et al., (1988) *Plant Mol. Biol.* 11: 717–729), bean lectin (Voelker et al., (1987) *EMBO J.* 6: 3571–3577), soybean lectin (Okamuro et al., (1986) *Proc. Natl. Acad. Sci. USA* 83: 8240–8244), soybean Kunitz trypsin inhibitor (Perez-Grau et al., (1989) *Plant Cell* 1: 095–1109), soybean b-conglycinin (Beachy et al., (1985) *EMBO J.* 4: 3047–3053; pea vicilin (Higgins et al., (1988) *Plant Mol. Biol.* 11:683–695), pea convicilin (Newbigin et al., (1990) *Planta* 180:461–470), pea legumin (Shirsat et al., (1989) *Mol. Gen. Genetics* 215:326–331); rapeseed napin (Radke et al., (1988) *Theor. Appl. Genet.* 75:685–694) as well as genes from monocotyledonous plants such as for maize 15 kD zein (Hoffman et al., (1987) *EMBO J.* 6:3213–3221), maize 18 kD oleosin (Lee at al., (1991) *Proc. Natl. Acad. Sci. USA* 88:6181–6185), barley β-hordein (Marris et al., (1988) *Plant Mol. Biol.* 10:359–366) and wheat glutenin (Colot et al., (1987) *EMBO J.* 6:3559–3564). Moreover, promoters of seed-specific genes operably linked to heterologous coding sequences in chimeric gene constructs also maintain their temporal and spatial expression pattern in transgenic plants. Such examples include use of *Arabidopsis thaliana* 2S seed storage protein gene promoter to express enkephalin peptides in Arabidopsis and *Brassica napus* seeds (Vandekerckhove et al., (1989) *Bio/Technology* 7:929–932), bean lectin and bean β-phaseolin promoters to express luciferase (Riggs et al., (1989) *Plant Sci.* 63:47–57), and wheat glutenin promoters to express chloramphenicol acetyl transferase (Colot et al., (1987) *EMBO J.* 6:3559–3564).

Of particular use in the expression of the nucleic acid fragment of the invention will be the heterologous soybean seed storage protein gene promoter from beta-conglycinin (Harada et al., (1989) *Plant Cell* 1:415–425). This promoter will be particularly useful for co-suppression in the cotyledons at mid- to late-stages of seed development (Beachy et al., (1985) *EMBO J.* 4: 3047–3053) in transgenic plants. This is because there is very little position effect on its expression in transgenic seeds. An added benefit of this promoter is realized because its use as a transgenic promoter is known to cause high frequency co-suppression of the endogenous beta-conglycinin protein. This protein is known to be a minor allergen in soybeans (Bush and Hefle (1996) *Critical Rev in Food Science and Nutrition* 36:S119–S163).

In a second embodiment, this invention concerns a recombinant expression construct for producing a hypoallergenic soybean which comprises an isolated KSTI nucleic acid fragment corresponding substantially to the nucleotide sequence set forth in SEQ ID NO:2 or a functionally equivalent subfragment thereof operably linked to an isolated Gly m Bd 28K nucleic acid fragment corresponding substantially to the nucleotide sequence set forth in SEQ ID NO:3 or a functionally equivalent subfragment thereof. A transgenic soybean plant which comprises at least one of the recombinant expression constructs, described herein, in its genome should be hypoallergenic with respect to one or more of the following allergens: P34, KSTI, and SII.

In a third embodiment, this invention concerns a hypoallergenic soybean plant comprising in its genome at least one of the expression constructs of this invention, seeds obtained from such plants, oil obtained from the seeds of these plants, products made from the hydrogenation, fractionation, interesterification or hydrolysis of oil obtained from the seeds of such plants, hypoallergenic soybean products, and any food or any feed incorporating any of the hypoallergenic soybean products or oils as described herein.

Such transgenic soybean plants can be made using conventional techniques well known to those skilled in the art as is discussed above. Introduction of transgenes into plants, i.e., transformation is well known to the skilled artisan. A preferred method of plant cell transformation is the use of particle-accelerated or "gene gun" transformation technology (Klein et al. (1978) *Nature* (*London*) 327:70–73; U.S. Pat. No. 4,945,050).

In a fourth embodiment, this invention concerns hypoallergenic soybean products obtained from transgenic soybean plants comprising at least one of the recombinant expression constructs of the invention in its genome. "Soy protein products" are defined as those items produced from soybean seed and are then used as ingredients in the production of any feed and any food, for example, breakfast cereals, in baking applications (e.g., breads, rolls, etc.), in dairy or meat based food products such as infant formula, nutritional beverage, milk replacer, soy extended bologna, imitation processed cheese spread, brine injected ham, yogurt and frozen desserts and the like. Table 1 lists a variety of soybean protein products derived from soybean seeds. The terms "soy protein products" and "soy products" are used interchangeably herein. Soy protein processing is depicted in FIG. 1.

TABLE 1

| Soy Protein Products Derived from Soybean Seeds[a] |
|---|
| Whole Soybean Products |
| Roasted Soybeans<br>Baked Soybeans<br>Soy Sprouts<br>Soy Milk |
| Speciality Soy Foods/Ingredients |
| Soy Milk<br>Tofu<br>Tempeh<br>Miso |

TABLE 1-continued

Soy Protein Products Derived from Soybean Seeds[a]

Soy Sauce
Hydrolyzed Vegetable Protein
Whipping Protein
Processed Soy Protein Products Soybean Meal
Soy Grits
Full Fat and Defatted Flours
Soy Protein Isolates
Soy Protein Concentrates
Textured Soy Proteins
Textured Flours and Concentrates
Structured Concentrates
Structured Isolates

[a]See Soy Protein Products: Characteristics, Nutritional Aspects and Utilization (1987). Soy Protein Council "Processing" refers to any physical and chemical methods used to obtain the products listed in Table 1 and includes, but is not limited to heat conditioning, flaking and grinding, extrusion, solvent extraction, or aqueous soaking and extraction of whole or partial seeds. Furthermore, "processing" includes the methods used to concentrate and isolate soy protein from whole or partial seeds, as well as the various traditional Oriental methods in preparing fermented soy food products. Trading Standards and Specifications have been established for many of these products (see National Oilseed Processors Association Yearbook and Trading Rules 1991–1992). Products referred to as being "high protein" or "low protein" are those as decribed by these Standard Specifications. "NSI" refers to the Nitrogen Solubility Index as defined by the American Oil Chemists' Society Method Ac4 41. "KOH Nitrogen Solubility" is an indicator of soybean meal quality and refers to the amount of nitrogen soluble in 0.036 M KOH under the conditions as described by Araba and Dale (1990) Poultry Science 69:76–83.

"White" flakes refer to flaked, dehulled cotyledons that have been defatted and treated with controlled moist heat to have an NSI of about 85 to 90. This term can also refer to a flour with a similar NSI that has been ground to pass through a No. 100 U.S. Standard Screen size. "Cooked" refers to a soy protein product, typically a flour, with an NSI of about 20 to 60. "Toasted" refers to a soy protein product, typically a flour, with an NSI below 20.

"Grits" refer to defatted, dehulled cotyledons having a U.S. Standard screen size of between No. 10 and 80. Soy flours and grits are made by grinding and screening soybean flakes either before or after removal of the oil. Their protein content is in the range of 40% to 54%. Soy flours and grits are the least refined forms of soy protein products used for human consumption and may vary in fat content, particle size, and degree of heat treatment. They are also produced in lecithinated or refatted forms. The degree of heat treatment creates varying levels of water dispersibility, a quality that can be useful in tailoring functionality in many food applications.

"Soy Protein Concentrates" refer to those products produced from dehulled, defatted soybeans by three basic processes: acid leaching (at about pH 4.5), extraction with alcohol (about 55–80%), and denaturing the protein with moist heat prior to extraction with water. Conditions typically used to prepare soy protein concentrates have been described by Pass (1975) U.S. Pat. No. 3,897,574; Campbell et al., (1985) in New Protein Foods, ed. by Altschul and Wilcke, Academic Press, Vol. 5, Chapter 10, Seed Storage Proteins, pp 302–338. Thus, term "soy protein concentrates" as used herein refers to those products which are prepared from high quality sound, clean dehulled soybean seeds by removing most of the oil and water soluble non-protein constituents and must contain not less than 65% protein on a moisture free basis as set forth in [(1966) Official Publication of the Association of American Feed Control Officials, Inc.]. Neutralized concentrates prepared by acid leaching have a higher water-soluble protein content than those prepared by either alcohol leaching or heat denaturation techniques. In another process, low water-soluble soy protein concentrate (aqueous alcohol extraction) is subjected to heat treatment by steam injection or jet cooking to increase solubility and functionality. Functionality may be improved further by additional treatments. Concentrates function as emulsifiers and emulsion stabilizers, they bind fat and water, and they offer special adhesive properties similar to those of isolates.

The term "soy protein isolates" as used herein refers to those products which are the major proteinaceous fraction of soybeans prepared from dehulled soybeans by removing the majority of non-protein compounds and must contain not less than 90% protein on a moisture free basis as set forth in [(1996) Official Publication of the Association of American Feed Control Officials, Inc.]. Isolates may also be lecithinated to improve disperisibility and to reduce dusting. Both gelling and non-gelling varieties are available, as well as varying grades of viscosity.

"Extrusion" refers to processes whereby material (grits, flour or concentrate) is passed through a jacketed auger using high pressures and temperatures as a means of altering the texture of the material. "Texturing" and "structuring" refer to extrusion processes used to modify the physical characteristics of the material. The characteristics of these processes, including thermoplastic extrusion, have been described previously [Atkinson, (1970) U.S. Pat. No. 3,488,770, Horan (1985) In New Protein Foods, ed. by Altschul and Wilcke, Academic Press, Vol. 1A, Chapter 8, pp 367–414]. Moreover, conditions used during extrusion processing of complex foodstuff mixtures that include soy protein products have been described previously [Rokey (1983) Feed Manufacturing Technology III, 222–237; McCulloch, U.S. Pat. No. 4,454,804].

Oil made from seeds obtained from the hypoallergenic soybean plants of the invention can be used in a variety of applications. These oils can be used in the preparation of foods. Examples include, but are not limited to, uses as ingredients, as coatings, as salad oils, as spraying oils, as roasting oils, and as frying oils. Foods in which the oil may be used include, but are not limited to, crackers and snack foods, confectionery products, syrups and toppings, sauces and gravies, soups, batter and breading mixes, baking mixes and doughs.

These oils can also be used as a blending source to make a blended oil product. By a blending source, it is meant that the oil of this invention can be mixed with other vegetable oils to improve the characteristics, such as fatty acid composition, flavor, and oxidative stability, of the other oils. The amount of oil of this invention which can be used will depend upon the desired properties sought to be achieved in the resulting final blended oil product. Examples of blended oil products include, but are not limited to, margarines, shortenings, frying oils, salad oils, etc.

In another aspect, the oils of this invention can be subjected to further processing such as hydrogenation, fractionation, interesterification or fat splitting (hydrolysis).

In still another aspect, this invention concerns by-products made during the production of the oils of this invention.

Methods for the extraction and processing of soybean seeds to produce soybean oil and meal are well known throughout the soybean processing industry. In general, soybean oil is produced using a series of steps that accomplish the extraction and purification of an edible oil product from the oil bearing seed. Soybean oils and soybean byproducts are produced using the generalized steps shown in the diagram below.

Soybean seeds are cleaned, tempered, dehulled, and flaked which increases the efficiency of oil extraction. Oil extraction is usually accomplished by solvent (hexane) extraction but can also be achieved by a combination of physical pressure and/or solvent extraction. The resulting oil is called crude oil. The crude oil may be degummed by hydrating phospholipids and other polar and neutral lipid complexes which facilitate their separation from the nonhydrating, triglyceride fraction (soybean oil). The resulting lecithin gums may be further processed to make commercially important lecithin products used in a variety of food and industrial products as emulsification and release (antisticking) agents.

Lecithin constitutes a member of a class of complex lipids called phospholipids, phosphoglycerides or glycerol phosphatides. They are characteristic major components of cell membranes. The most abundant phospholipids in higher plants and animals are phosphatidylcholine and phosphatidylethanolamine which contain as head groups the amino alcohols ethanolamine and choline, respectively. (The new names recommended for these phosphoglycerides are phosphatidylcholine and phosphatidylethanolamine. The old trivial names are lecithin and cephalin, respectively). These two phosphoglycerides are major components of most animal cell membranes. The so-called lecithin products described above are actually a mixture of phospholipids, predominantly phosphatidylcholine and phosphatidylethanolamine.

Degummed oil may be further refined for the removal of impurities; primarily free fatty acids, pigments, and residual gums. Refining is accomplished by the addition of caustic which reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth which removes most of the chlorophyll and carotenoid compounds. The refined oil can be hydrogenated resulting in fats with various melting properties and textures. Winterization (fractionation) may be used to remove stearine from the hydrogenated oil through crystallization under carefully controlled cooling conditions. Deodorization which is principally steam distillation under vacuum, is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, (1995) Practical Handbook of Soybean Processing and Utilization, The American Oil Chemists' Society and United Soybean Board.

Hydrogenation is a chemical reaction in which hydrogen is added to the unsaturated fatty acid double bonds with the aid of a catalyst such as nickel. High oleic soybean oil contains unsaturated oleic, linoleic, and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction which in turn alter the composition of the final product. Operating conditions including pressure, temperature, catalyst type and concentration, agitation and reactor design are among the more important parameters which can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings, used in the manufacture of baking products, solid fats and shortenings used for commercial frying and roasting operations, and base stocks for margarine manufacture are among the myriad of possible oil and fat products achieved through hydrogenation. A more detailed description of hydrogenation and hydrogenated products can be found in Patterson, H. B. W., (1994) Hydrogenation of Fats and Oils: Theory and Practice. The American Oil Chemists' Society.

Interesterification refers to the exchange of the fatty acyl moiety between an ester and an acid (acidolysis), an ester and an alcohol (alcoholysis) or an ester and ester (transesterification). Interesterification reactions are achieved using chemical or enzymatic processes. Random or directed transesterification processes rearrange the fatty acids on the triglyceride molecule without changing the fatty acid composition. The modified triglyceride structure may result in a fat with altered physical properties. Directed interesterification reactions using lipases are becoming of increasing interest for high value specialty products like cocoa butter substitutes. Products being commercially produced using interesterification reactions include but are not limited to shortenings, margarines, cocoa butter substitutes and structured lipids containing medium chain fatty acids and polyunsaturated fatty acids. Interesterification is further discussed in Hui, Y. H., (1996) Bailey's Industrial Oil and Fat Products, Volume 4, John Wiley & Sons.

Fatty acids and fatty acid methyl esters are two of the more important oleochemicals derived from vegetables oils. Fatty acids are used for the production of many products such as soaps, medium chain triglycerides, polyol esters, alkanolamides, etc. Vegetable oils can be hydrolyzed or split into their corresponding fatty acids and glycerine. Fatty acids produced from various fat splitting processes may be used crude or more often are purified into fractions or individual fatty acids by distillation and fractionation. Purified fatty acids and fractions thereof are converted into a wide variety of oleochemicals, such as dimer and trimer acids, diacids, alcohols, amines, amides, and esters. Fatty acid methyl esters are increasingly replacing fatty acids as starting materials for many oleochemicals such as fatty alcohols, alkanolamides, α-sulfonated methyl esters, diesel oil components, etc. Glycerine is also obtained by the cleavage of triglycerides using splitting or hydrolysis of vegetable oils. Further references on the commercial use of fatty acids and oleochemicals may be found in Erickson, D. R., (1995) Practical Handbook of Soybean Processing and Utilization, The American Oil Chemists' Society, and United Soybean Board; Pryde, E. H., (1979) Fatty Acids, The American Oil Chemists' Society; and Hui, Y. H., (1996) Bailey's Industrial Oil and Fat Products, Volume 4, John Wiley & Sons.

In a fifth embodiment, this invention concerns a method of producing a hypoallergenic soy product from hypoallergenic soybean seeds which comprises:
  (a) cracking the seeds obtained from a hypoallergenic soybean plant comprising in its genome at least one of the recombinant constructs of the invention to remove the meats from the hulls; and
  (b) flaking the meats obtained in step (a) to obtain the desired flake thickness.

In a sixth embodiment, this invention concerns a method for making a hypoallergenic soybean plant which comprises:
  (a) crossing a first parent soybean which is a soybean plant comprising in its genome recombinant expression construct to lower the Gly m Bd 30K (Soybean vacuolar protein P34) content of a soybean which comprises a beta-conglycinin promoter operably linked to an isolated Gly m Bd 30K nucleic acid fragment corresponding substantially to the nucleotide sequence set forth in SEQ ID NO:1 or a functionally equivalent subfragment thereof, with a second soybean parent which is substantially free of one or more allergens selected from the group consisting Gly m Bd 28K, alpha-subunit of beta-conglycinin, KSTI, Gly m2, Gly m IA, Gly m IB, rGLY m3 and Glycinin G1; and
  (b) selecting progeny plants of the cross of step (a) which are hypoallergenic.

A hypoallergenic soybean plant made by this method, seeds obtained therefrom, oil obtained from the seeds, soybean protein products obtained from such seeds and any food or feed which incorporates such soybean protein products or oil should be hypoallergenic with respect to one or more of the following, P34 a major soybean allergen, and the minor soybean protein allergens Gly m Bd 28K, alpha-subunit of beta-conglycinin, KSTI, Gly m2, Gly m IA, Gly m IB, rGLY m3 and glycinin G1.

In a seventh embodiment, this invention concerns a method for making a hypoallergenic soybean plant which comprises:
  (a) crossing a first parent soybean which is a soybean plant comprising in its genome a recombinant expression construct to lower the Gly m Bd 30K (Soybean vacuolar protein P34) content of a soybean which comprises a beta-conglycinin promoter operably linked to an isolated Gly m Bd 30K nucleic acid fragment corresponding substantially to the nucleotide sequence set forth in SEQ ID NO:1 or a functionally equivalent subfragment thereof, with a second soybean parent which is naturally occurring soybean mutant which is substantially free of Gly m Bd 28K and which is substantially free of the alpha-subunit of beta-conglycinin; and
  (b) selecting progeny plants of the cross of step (a) which are hypoallergenic.

A hypoallergenic soybean plant made by this method, seeds obtained therefrom, oil obtained from the seeds, soybean protein products obtained from such seeds and any food or feed which incorporates such soybean protein products or oil should be hypoallergenic with respect to one or more of the following, P34 a major soybean allergen, and the minor soybean protein allergens Gly m Bd 28K and the alpha-subunit of beta-conglycinin.

In an eighth embodiment, this invention concerns a method for making a hypoallergenic soybean plant which comprises:
  (a) crossing a first parent soybean which is the soybean plant comprising in its genome at least one of the recombinant constructs of the invention with a second soybean parent wherein the second parent is selected from the group consisting of a soybean plant comprising in its genome a recombinant expression construct which produces a lower level of the alpha subunit of beta-conglycinin or a naturally occuring variant thereof; and
  (b) selecting progeny plants of the cross of step (a) which are hypoallergenic.

A hypoallergenic soybean plant made by this method, seeds obtained therefrom, oil obtained from the seeds, soybean protein products obtained from such seeds and any food or feed which incorporates such soybean protein products or oil should be hypoallergenic with respect to the major soybean allergen P34, and the minor soybean protein allergens 68-K (the a subunit of b-conglycinin), KSTI (KTi3), Gly m2, Gly m IA, Gly m IB, rGLY m3, and glycinin G1.

In a ninth embodiment, this invention concerns a method for making a hypoallergenic soybean plant which comprises:
  (a) crossing a first parent soybean which is the soybean plant comprising in its genome at least one of the recombinant constructs of the invention with a second soybean parent wherein the second parent comprises naturally occurring mutant soybean plants which are substantially free of the KSTI allergen; and
  (b) selecting progeny plants of the cross of step (a) which are hypoallergenic.

A hypoallergenic soybean plant made by this method, seeds obtained therefrom, oil obtained from the seeds, soybean protein products obtained from such seeds and any food or feed which incorporates such soybean protein products or oil should be hypoallergenic with respect to the major soybean allergen P34, and the minor soybean protein allergens 68-K (the a subunit of β-conglycinin), KSTI (KTi3), Gly m2, Gly m IA, Gly m IB, rGLY m3, and glycinin G1.

Also of interest, are seeds obtained from such plants, oil obtained from these seeds, soybean protein products obtained from such seeds and any food or feed which incorporates such soy protein product or oil as well as any products made from the hydrogenation, fractionation, interesterification or hydrolysis of oil obtained from the seeds of such plants.

In a tenth embodiment, this invention concerns an isolated nucleic acid fragment comprising a nucleic acid sequence encoding a soybean Gly m Bd 28K protein. The protein which is encoded by the nucleic acid fragment can have an amino acid identity of 49% or greater to the polypeptide sequence set forth in SEQ ID NO:4 or a functionally equivalent subfragment thereof.

In another aspect, this isolated nucleic acid fragment can have a nucleic acid identity of 48% or greater to the sequence set forth in SEQ ID NO:3.

Also of interest is any plant protein, similar to Gly m Bd 28K protein, having an amino acid identity of 49% or greater to the polypeptide encoded by SEQ ID NO:4. Plant proteins of interest would include, but not be limited to, seed-storage proteins, proteins exhibiting modifications such as glycosylation, or allergenic proteins.

Chimeric genes comprising such nucleic acid fragments or the reverse complement thereof operably to regulatory sequences are also of interest as well as hypoallergenic soybean plants comprising such chimeric genes, seeds obtained from such plants, oil obtained from such seeds, and products made from the hydrogenation, fractionation, interesterification or hydrolysis of oil obtained from the seeds of such plants. In still another aspect, this invention concerns a hypoallergenic soybean product, and any food or any feed incorporating this soybean product or oil.

Hypoallergenic soybean products are discussed above. Such products include, but are not limited to, isolates, concentrates, meal, grits, full fat and defatted flours, textured proteins, textured flours, textured concentrates and textured isolates.

In an eleventh embodiment, this invention concerns an isolated nucleic acid fragment comprising a nucleic acid sequence encoding a soybean Gly m 2 protein. The protein which is encoded can have an amino acid identity of 95% or greater to the polypeptide sequence set forth in SEQ ID NO:6 or a functionally equivalent subfragment thereof.

In another aspect, this isolated nucleic acid fragment can have a nucleic acid identity of 70% or greater to the sequence set forth in SEQ ID NO:5. Also of interest is any plant Gly m 2 protein having an amino acid identity of 95% or greater to the polypeptide sequence set forth in SEQ ID NO:4. Chimeric genes comprising such nucleic acid fragments or the reverse complement thereof operably to regulatory sequences are also of interest as well as hypoallergenic soybean plants comprising such chimeric genes, seeds obtained from such plants, oil obtained from such seeds, and products made from the hydrogenation, fractionation, interesterification or hydrolysis of oil obtained from the seeds of such plants. In still another aspect, this invention concerns a hypoallergenic soybean product, and any food or any feed incorporating this soybean product or oil as is discussed above.

In a twelfth embodiment, this invention concerns a recombinant expression construct to lower Gly m IB content of a soybean which comprises a promoter operably linked to an isolated Gly m IB nucleic acid fragment corresponding substantially to the nucleotide sequence set forth in SEQ ID NO:9 or a functionally equivalent subfragment thereof.

In a thirteenth embodiment, this invention concerns a recombinant expression construct to lower Gly m IB content of a soybean which comprises a promoter operably linked to an isolated Gly m IB nucleic acid fragment corresponding substantially to the nucleotide sequence set forth in SEQ ID NO:9 or a functionally equivalent subfragment thereof.

In a fourteenth embodiment, this invention concerns a recombinant expression construct to lower rGLY m3 content of a soybean wherein which comprises a promoter operably linked to an isolated rGly m3 nucleic acid fragment corresponding substantially to the nucleotide sequence set forth in SEQ ID NOs:11 and 13 or a functionally equivalent subfragment thereof.

In a fifteenth embodiment, this invention concerns a recombinant expression construct to lower Glycinin G1 (AlaB1b) content of a soybean wherein which comprises a promoter operably linked to an isolated Glycinin G1 nucleic acid fragment corresponding substantially to the nucleotide sequence set forth in SEQ ID NO:15 or a functionally equivalent subfragment thereof.

Also of interest are a hypoallergenic soybean plant comprising in its genome at least one of the claimed recombinant expression constructs. Also of interest are seeds obtained from such plants, oil obtained from these seeds and products made from the hydrogenation, fractionation, interesterification or hydrolysis of oil obtained from the seeds of such plants. In still another aspect, this invention concerns a hypoallergenic soybean product, and any food or any feed incorporating this soybean product or oil.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. The disclosures contained within the references used herein are hereby incorporated by reference.

Example 1

Alteration of Gly m 1 Content of Soybean Somatic Embryos

The ability to change the Gly m 1 content of soybean embryos by gene suppression was tested by preparing transgenic soybean somatic embryos and assaying the isoflavone levels. The entire insert from Genbank clone J05560 was amplified in a standard PCR reaction on a Perkin Elmer Applied Biosystems GeneAmp PCR System using Pfu polymerase (Stratagene) with the primers shown in SEQ ID NO:7 and SEQ ID NO:8:

5'-GAATT<u>CGCGGCCGC</u>ATGGGTTTCCTTGTGT-3'  [SEQ ID NO:7]

5'-GAATT<u>CGCGGCCGC</u>TCAAAGAGGAGAGTGA-3'  [SEQ ID NO:8]

Figure 4:
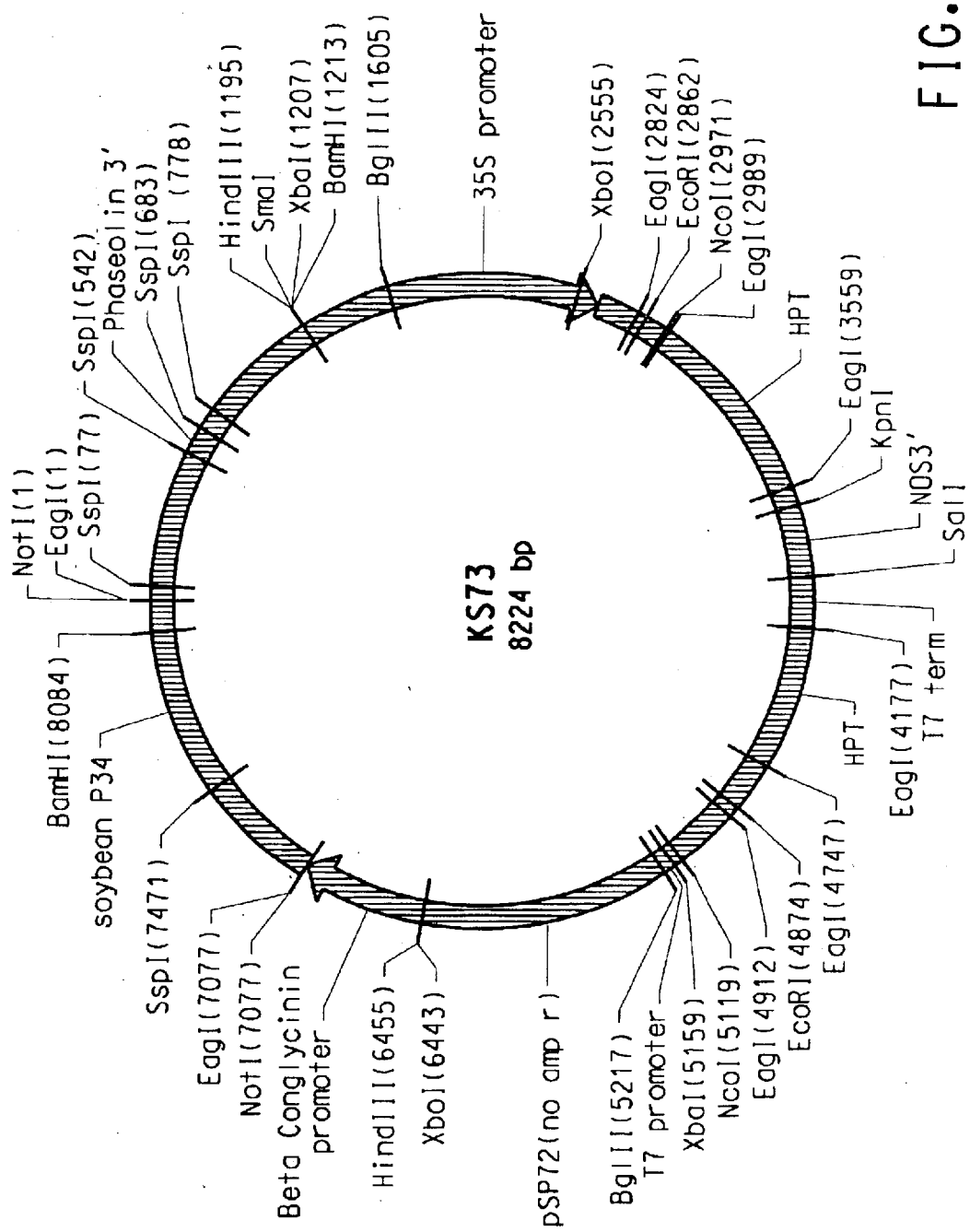
FIG. 4 is a map of plasmid pKS73 containing the Gly m 1 gene in sense orientation to the promoter from the α'-subunit of beta-conglycinin and followed by the phaseolin 3' untranslated region. This plasmid was used in the co-suppression experiments outlined in Example 1.

The resulting fragment is bound by Not I sites in the primer sequences (underlined above) and contains a 5' leader sequence, the coding region for Gly m 1, the untranslated 3' region from SEQ ID NO: and a stretch of 18 A residues at the 3' end. This fragment was digested with Not I and ligated to Not I-digested and phosphatase-treated pKS67. The plasmid pKS67 was prepared from pRB20 (U.S. Pat. No. 5,846,784) by replacing the 800 bp nopaline synthase 3' untranslated region (Nos 3') with a shorter 285 bp Nos 3' fragment. Both Nos 3' fragments contain the polyadenylation signal sequence (Depicker A. et al., (1982) *J. Mol. Appl. Genet.* 1:561–573). Clones were screened for the sense orientation of the Gly 1 m insert fragment by digestion with Bam HI. The resulting plasmid pKS73, shown in FIG. 4, has the beta-conglycinin promoter operably linked to the fragment encoding Gly 1 m followed by the Nos 3'end. Plasmid pKS73 contains a T7 promoter/HPT/T7 terminator cassette for expression of the HPT enzyme in certain strains of *E. coli*, such as NovaBlue (DE3) (from Novagen), that are lysogenic for lambda DE3 (which carries the T7 RNA Polymerase gene under lacV5 control). Plasmid pKS73 also contains the 35S/HPT/NOS 3' cassette for constitutive expression of the HPT enzyme in plants. These two expression systems allow selection for growth in the presence of hygromycin to be used as a means of identifying cells that contain plasmid DNA sequences in both bacterial and plant systems.

Example 2

Transformation of Somatic Soybean Embryo Cultures

Soybean embryogenic suspension cultures were maintained in 35 ml liquid media (SB55 or SBP6) on a rotary shaker, 150 rpm, at 28° C. with mixed fluorescent and incandescent lights on a 16:8 h day/night schedule. Cultures were subcultured every four weeks by inoculating approximately 35 mg of tissue into 35 ml of liquid medium.

TABLE 2

Stock Solutions (g/L):

| MS Sulfate 100X Stock | | SB55 (per Liter, pH 5.7) |
|---|---|---|
| $MgSO_4$ $7H_2O$ | 37.0 | 10 mL each MS stocks |
| $MnSO_4$ $H_2O$ | 1.69 | 1 mL B5 Vitamin stock |
| $ZnSO_4$ $7H_2O$ | 0.86 | 0.8 g $NH_4NO_3$ |
| $CuSO_4$ $5H_2O$ | 0.0025 | 3.033 g $KNO_3$ |
| MS Halides 100X Stock | | 1 mL 2,4-D (10 mg/mL stock) |
| $CaCl_2$ $2H_2O$ | 44.0 | 60 g sucrose |
| KI | 0.083 | 0.667 g asparagine |
| $CoCl_2$ $6H_2O$ | 0.00125 | SBP6 |
| $KH_2PO_4$ | 17.0 | same as SB55 except 0.5 |
| $H_3BO_3$ | 0.62 | mL 2,4-D |
| $Na_2MoO_4$ $2H_2O$ | 0.025 | SB103 (per Liter, pH 5.7) |
| MS FeEDTA 100X Stock | | 1X MS Salts |
| $Na_2EDTA$ | 3.724 | 6% maltose |
| $FeSO_4$ $7H_2O$ | 2.784 | 750 mg $MgCl_2$ |
| B5 Vitamin Stock | | 0.2% Gelrite |
| 10 g m-inositol | | SB71-1 (per Liter, pH 5.7) |
| 100 mg nicotinic acid | | 1X B5 salts |
| 100 mg pyridoxine HCl | | 1 ml B5 vitamin stock |
| 1 g thiamine | | 3% sucrose |
| | | 750 mg $MgCl_2$ |
| | | 0.2% Gelrite |

Soybean embryogenic suspension cultures were transformed with pTC3 by the method of particle gun bombardment (Kline et al. (1987) *Nature* 327:70). A DuPont Biolistic PDS 1000/HE instrument (helium retrofit) was used for these transformations.

To 50 ml of a 60 mg/ml 1 mm gold particle suspension was added (in order); 5 µl DNA(1 µg/µl), 20 µl spermidine (0.1 M), and 50 µl $CaCl_2$ (2.5 M). The particle preparation was agitated for 3 min, spun in a microfuge for 10 sec and the supernatant removed. The DNA-coated particles were then washed once in 400 µl 70% ethanol and re suspended in 40 µl of anhydrous ethanol. The DNA/particle suspension was sonicated three times for 1 sec each. Five µl of the DNA-coated gold particles were then loaded on each macro carrier disk.

Approximately 300–400 mg of a four week old suspension culture was placed in an empty 60×15 mm petri dish and the residual liquid removed from the tissue with a pipette. For each transformation experiment, approximately 5–10 plates of tissue were normally bombarded. Membrane rupture pressure was set at 1000 psi and the chamber was evacuated to a vacuum of 28 inches of mercury. The tissue was placed approximately 3.5 inches away from the retaining screen and bombarded three times. Following bombardment, the tissue was placed back into liquid and cultured as described above.

Eleven days post bombardment, the liquid media was exchanged with fresh SB55 containing 50 mg/ml hygromycin. The selective media was refreshed weekly. Seven weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Thus each new line was treated as independent transformation event. These suspensions can then be maintained as suspensions of embryos clustered in an immature developmental stage through subculture or regenerated into whole plants by maturation and germination of individual somatic embryos.

Three lines of transformed embryogenic clusters (3/1, 6/1, and 7/1) were removed from liquid culture and placed on a solid agar media (SB 103) containing no hormones or antibiotics. Embryos were cultured for four weeks at 26° C. with mixed fluorescent and incandescent lights on a 16:8 h day/night schedule. During this period, individual embryos were removed from the clusters and screened for their lack of allergenic proteins by protein blot analysis (Example 4).

Example 3

The Phenotype of Transgenic Soybean Somatic Embryos is Predictive of Seed Phenotypes from Resultant Regenerated Plants Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α' subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis somatic soybean embryo system behaves very similarly to maturing zygotic soybean embryos in vivo, and is therefore a good and rapid model system for analyzing the phenotypic effects of modifying the expression of genes in the fatty acid biosynthesis pathway.

Most importantly, the model system is also predictive of the fatty acid composition of seeds from plants derived from transgenic embryos. This is illustrated with two different antisense constructs in two different types of experiment that were constructed following the protocols set forth in the PCT Publication Nos. WO 93/11245 and WO 94/11516. Liquid culture globular embryos were transformed with a chimeric gene comprising a soybean microsomal $\Delta^{15}$ desaturase as described in PCT Publication No. WO 93/11245 which was published on Jun. 10, 1993, the disclosure of which is hereby incorporated by reference (experiment 1,) or a soybean microsomal $\Delta^{12}$ desaturase as described in PCT Publication No. WO 94/11516 which was published on May 26, 1994, the disclosure of which is hereby incorporated by reference (experiment 2). Both gene constructs were introduced in antisense orientation under the control of a seed-specific promoter (β-conglycinin promoter) and gave rise to mature embryos. The fatty acid content of mature somatic embryos from lines transformed with vector only (control) and the vector containing the antisense chimeric genes as well as of seeds of plants regenerated from them was determined.

In experiment 1, one set of embryos from each line was analyzed for fatty acid content and another set of embryos from that same line was regenerated into plants.

In experiment 2, different lines, containing the same antisense construct, were used for fatty acid analysis in somatic embryos and for regeneration into plants. In experiment 1, in all cases where a reduced 18:3 content was seen in a transgenic embryo line, compared with the control, a reduced 18:3 content was also observed in segregating seeds of plants derived from that line, when compared with the control seed (Table 3).

In experiment 2, about 55% of the transformed embryo lines showed an increased 18:1 content when compared with control lines (Table 4). Soybean seeds, of plants regenerated from different somatic embryo lines containing the same antisense construct, had a similar frequency (53%) of high oleate transformants as the somatic embryos (Table 4). On occasion, an embryo line may be chimeric. That is, 10–70% of the embroys in a line may not contain the transgene. The remaining embryos which do contain the transgene, have been found in all cases to be clonal. In such a case, plants with both wild type and transgenic phenotypes may be regenerated from a single, transgenic line, even if most of the embryos analyzed from that line had a transgenic phenotype. An example of this is shown in Table 5, in which, of 5 plants regenerated from a single embryo line, 3 have a high oleic phenotype and two were wild type. In most cases, all the plants regenerated from a single transgenic line will have seeds containing the transgene. Thus, it was concluded that an altered fatty acid phenotype observed in a transgenic, mature somatic embryo line is predictive of an altered fatty acid composition of seeds of plants derived from that line.

TABLE 3

Percent 18:3 Content Of Embryos and Seeds of Control and $\Delta^{15}$ Antisense Construct Transgenic Soybean Lines

| Transformant Line | Embryo Average (SD, n = 10) | Seed Average (SD, n = 10) |
| --- | --- | --- |
| Control | 12.1 (2.6) | 8.9 (0.8) |
| $\Delta^{15}$ antisense, line 1 | 5.6 (1.2) | 4.3 (1.6) |
| $\Delta^{15}$ antisense, line 2 | 8.9 (2.2) | 2.5 (1.8) |
| $\Delta^{15}$ antisense, line 3 | 7.3 (1.1) | 4.9 (1.9) |
| $\Delta^{15}$ antisense, line 4 | 7.0 (1.9) | 2.4 (1.7) |
| $\Delta^{15}$ antisense, line 5 | 8.5 (1.9) | 4.5 (2.2) |
| $\Delta^{15}$ antisense, line 6 | 7.6 (1.6) | 4.6 (1.6) |

*[Seeds which were segregating with wild-type phenotype and without a copy of the transgene are not included in these averages]

TABLE 4

Oleate Levels in Somatic Embryos and Seeds of Regenerated Soybeans Transformed With, or Without, $\Delta^{12}$ Desaturase Antisense Construct

| | # of Vector Lines | # of Lines with High 18:1 | Average* % 18:1 |
| --- | --- | --- | --- |
| Somatic embryos: | | | |
| Control | 19 | 0 | 12.0 |
| $\Delta^{12}$ antisense | 20 | 11 | 35.3 |
| Seeds of regenerated plants: | | | |
| Control | 6 | 0 | 18.2 |
| $\Delta^{12}$ antisense | 17 | 9 | 44.4 |

*average 18:1 of transgenics is the average of all embryos or seeds transformed with the $\Delta^{12}$ antisense construct in which at least one embryo or seed from that line had an 18:1 content greater than 2 standard deviations from the control value (12.0 in embryos, 18.2 in seeds). The control average is the average of embryos or seeds which do not contain any transgenic DNA but have been treated in an identical manner to the transgenics.

TABLE 5

Analysis of Seeds From Five Independent Plants Segregating From Plant Line 4

| Plant # | Average seed 18:1% | Highest seed 18:1% |
| --- | --- | --- |
| 1 | 18.0 | 26.3 |
| 2 | 33.6 | 72.1 |
| 7 | 13.6 | 21.2 |
| 9 | 32.9 | 57.3 |
| 11 | 24.5 | 41.7 |

Mean of 15–20 seeds from 5 different plants regenerated from a single embryo line. Only plants #2, 9 and 11 have seeds with a high 18:1 phenotype.

Example 4

Assay for Gly 1 m Content of Transformed Embryos

Antibodies to Gly 1 m were those described in Herman, E. M., Melroy, D. L., Buckhout T. J. (1990) *Plant Physiol* 94:341–349 the disclosure of which is hereby incorporated by reference.

Transgenic embryos described in Example 2 were frozen in liquid nitrogen ground in a mortar with sample buffer (0.125 M Tris-HCl, Ph 6.8, containing 0.4% SDS, 20% glycerol, 4% SDS, 0.2% 2-mercaptoethanol) at a ratio of 1:5 (w/v). The solubilized proteins were heated to 70° C. and run on a standard SDS polyacrylamide gel (Sambrook et al. (1989) "Molecular Cloning" Cold Spring Harbor Laboratory Press, Cold Spring Harbor, N.Y.). The resolved proteins were transferred to a nitrocellulose membrane by standard electrotransfer. The membrane was treated with 3% gelatin solution to block non-specific binding. The filter was then incubated for 90 min with a 1:5000 dilution of antibody-containing clarified ascites fluid (described in the Herman reference cited above) in TBS (Tris-HCl, 2.42 g/l, pH 7.5, NaCl 29.2 g/l) with 1% gelatin. The membrane was washed with TBS, then incubated with a 1:5000 dilution of anti-mouse IgG-alkaline phosphatase (Sigma). The membrane was washed with TBS, and finally visualized with 1,2 dioexetane-phosphate luminescent detection as described in Ausubel et al (1999) *Current Protocols in Molecular Biology*, Vol. 2. pp 10.8.13 to 10.8.16.

Figures 1, 2:
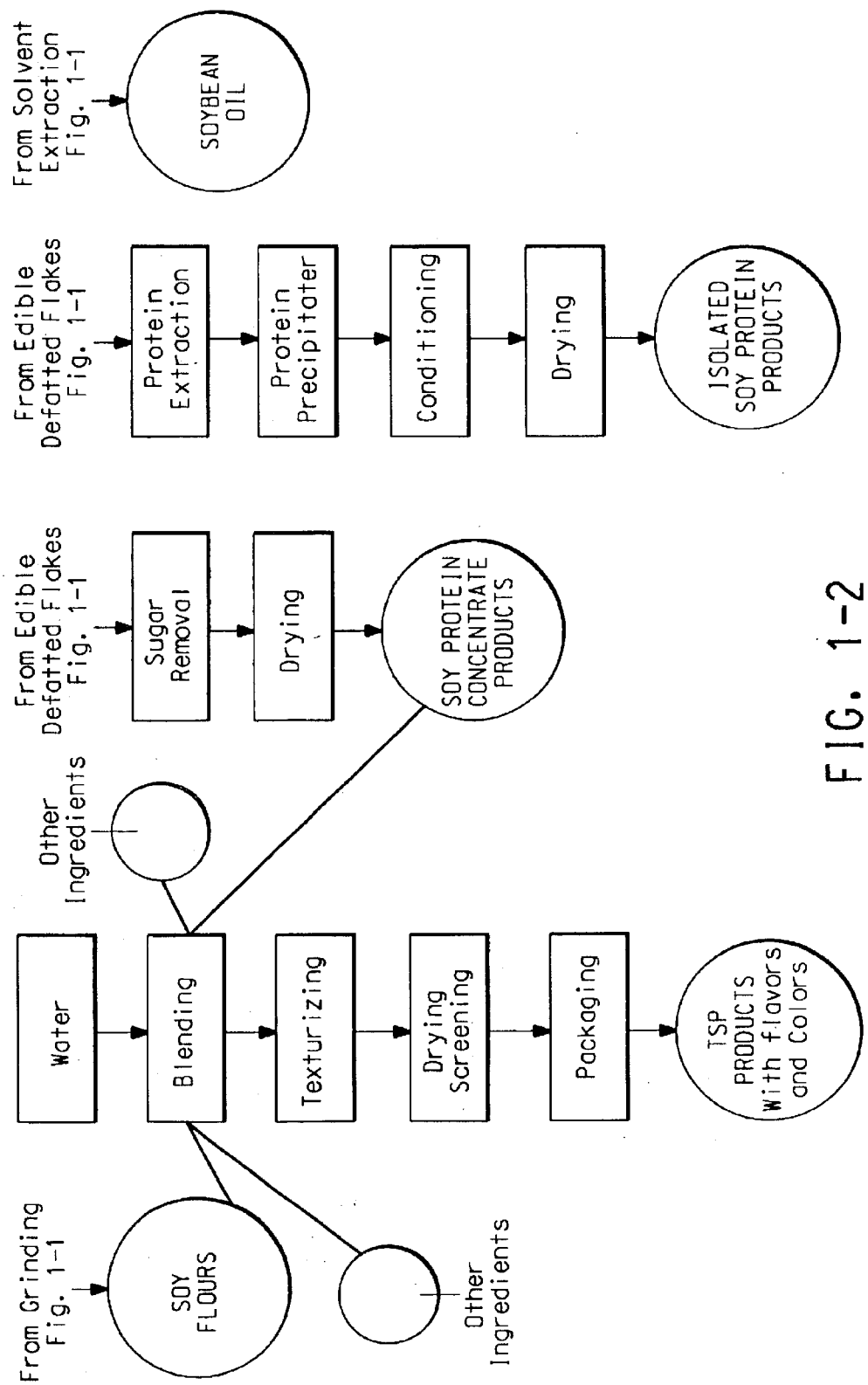
Figure 2:
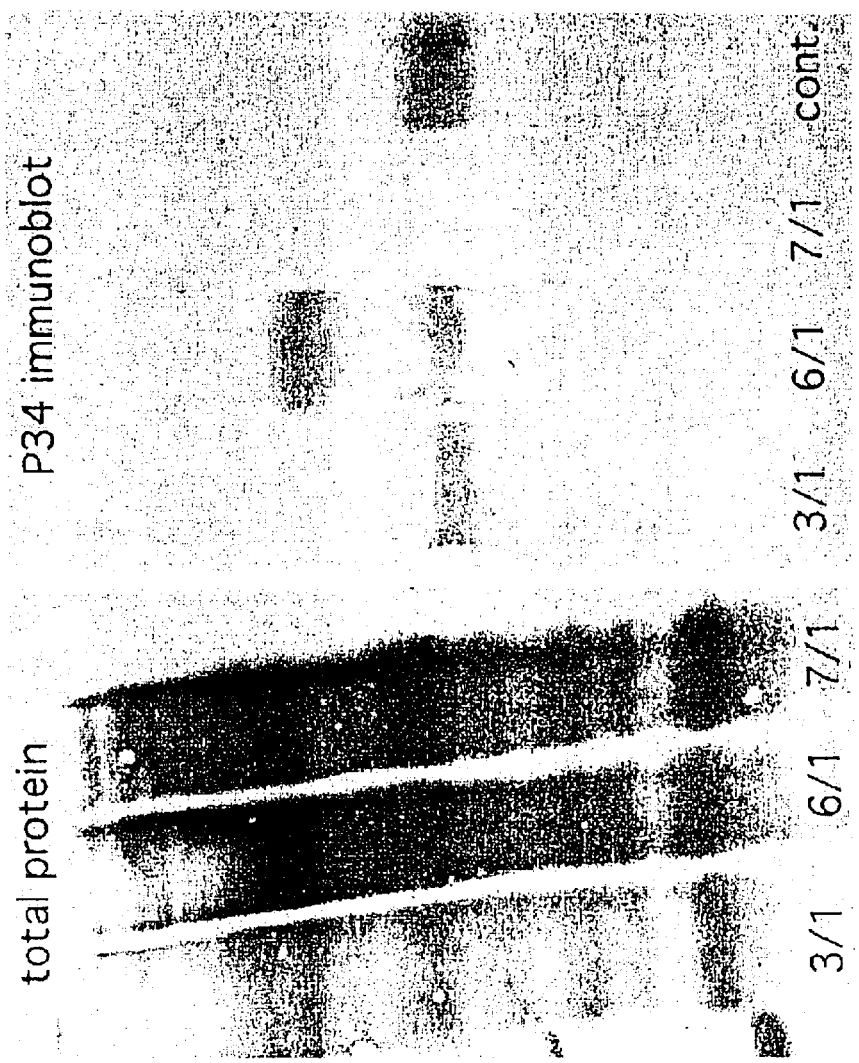

The results of an assay are shown in FIG. 2. Three independently transformed soybean embryos (3/1, 6/1, and 7/1), described in Example 2 above, were tested for the presence of the Gly 1m protein. The left panel shows the total protein loaded on each lane and the right panel shows the results of the antibody binding. The 7/1 embryo has no detectable Gly 1 m protein, unlike the other two embryos. A control for the Gly 1 m protein is shown on the right lane.

Example 5

Composition of cDNA Libraries: Isolation and Sequencing of cDNA Clones cDNA libraries representing mRNAs from various soybean tissues were prepared. The characteristics of the libraries are described below.

TABLE 6 cDNA Libraries from Soybean

| Library | Tissue | Clone |
|---|---|---|
| se6 | Soybean Embryo, 26 Days After Flowering | se6.pk0050.c3 |
| sls1c | Soybean Infected With *Sclerotinia sclerotiorum* mycelium | sls1c.pk027.a11 | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 6

Identification of cDNA Clones cDNA clones encoding soybean allergens were identified by conducting BLAST (Basic Local Alignment Search Tool; Altschul et al. (1993) *J. Mol. Biol.* 215:403–410; see also searches for similarity to sequences contained in the BLAST "nr" database (comprising all non-redundant GenBank COS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 7

Characterization of cDNA Clones Encoding Gly m Bd 28K and Gly m2

The BLASTX search using the EST sequences from clones listed in Table 6 revealed similarity of the polypeptides encoded by the cDNAs to soybean allergens from *Arabidopsis thaliana* for Gly mBd 28K (se6.pk0050.c3, SEQ ID NO:4) and cowpea [*Vigna unguiculata*] for Gly m2 (sls1c.pk027.a11, SEQ ID NO:6) (NCBI Accession Nos. gi 4510397 and gi 112671, respectively). Shown in Table 7 are the BLAST results for the cDNA sequences:

TABLE 7

BLAST Results for Sequences Encoding Polypeptides Homologous to Soybean Allergens

| Clone | BLAST pLog Score gi 4510397 | BLAST pLog Score gi 112671 |
|---|---|---|
| se6.pk0050.c3 | 115.00 | — |
| sls1c.pk027.a11 | — | 38.70 |

The data in Table 8 represents a calculation of the percent identity of the amino acid sequences set forth in SEQ ID NOs:4 and 6 and the Arabidopsis and cowpea proteins (respectively).

TABLE 8

Percent Identity of Amino Acid Sequences Deduced From the Nucleotide Sequences of cDNA Clones Encoding Polypeptides Homologous to Soybean Allergens

| SEQ ID NO. | Percent Identity to gi 4510397 | Percent Identity to gi 112671 |
|---|---|---|
| 4 | 46.7 | — |
| 6 | — | 93.3% |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a soybean allergen.

Example 8

Figure 5:
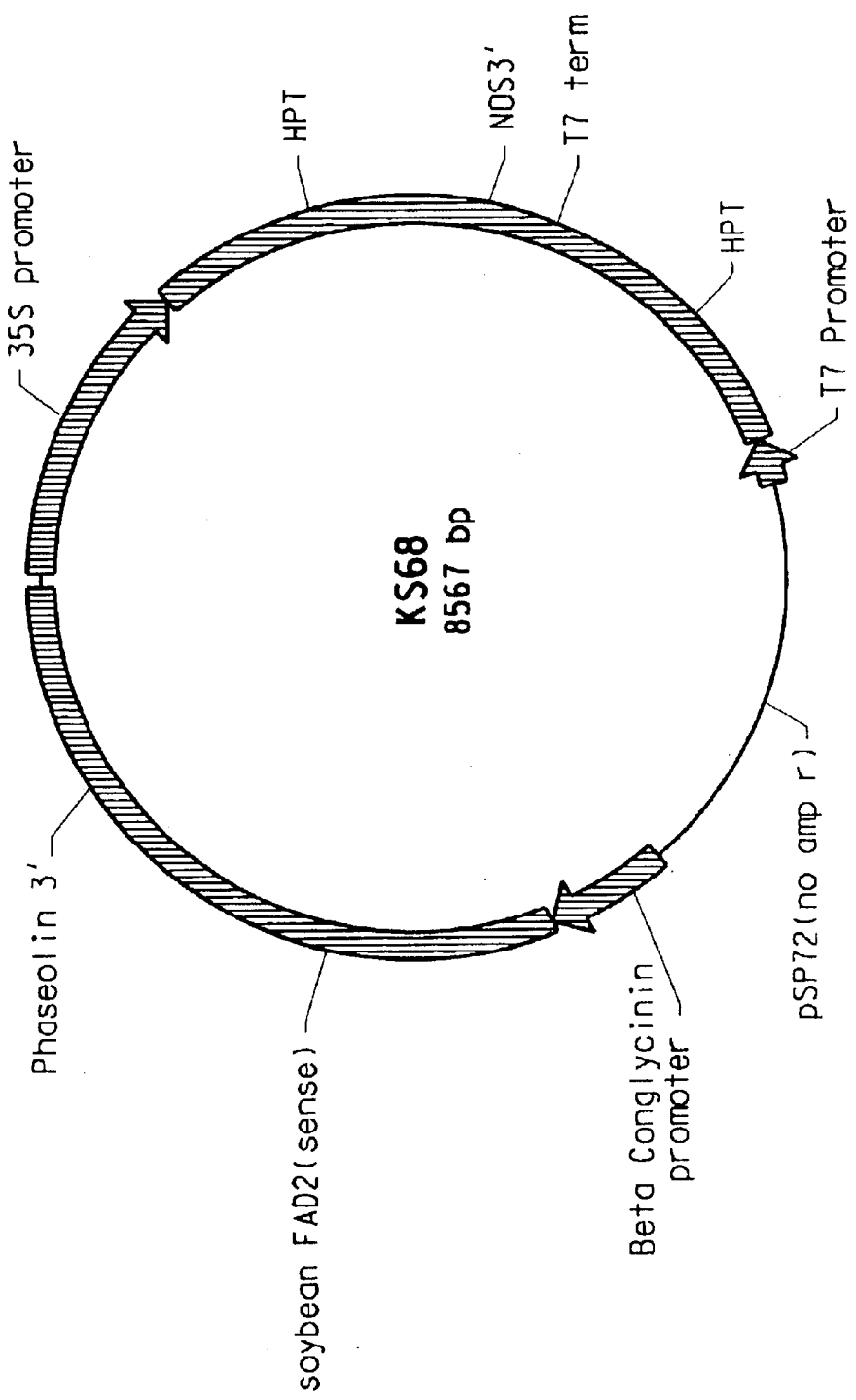
FIG. 5 is a map of plasmid pKS68 containing the Fad2 gene in sense orientation to the promoter from the α'-subunit of beta-conglycinin and followed by the phaseolin 3' untranslated region. This plasmid was used in the co-suppression experiments outlined in Example 8.

Coordinated Loss of Both α- and α'-Subunits of Beta-Conglycinin in Co-Suppressed Transgenic Plants It is believed that the use of recombinant expression constructs containing the promoter for the α'-subunit of beta conglycinin can result in the co-suppression of the gene encoding polypeptides for both the α- and α'-subunits of beta-conglycinin (PCT Publication No. WO 97/47731, as cited above). The construct pKS68 (FIG. 5) carrying the delta-12 desaturase (Fad2) gene coding region (described in detail by Okuley, J. et al. (1994) *Plant Cell* 6:147–158 and in the PCT Publication WO 94/11516, cited above) is under the control of the same beta-conglycinin promoter used in Example 1. PKS68 was used to generate soybean lines co-suppressing the Fad2 locus, according to protocols outlined in Example 2. Fad2, and its gene product, are responsible for the synthesis of the polyunsaturated fatty acids found in soybean oil (see Okuley, and WO 94/11516, cited above). Further descriptions of Fad2 and its use in altering soybean oil composition can be found in PCT Publication No. WO 97/40698, published Nov. 11, 1997, the disclosure of which is hereby incorporated by reference.

Figure 3:
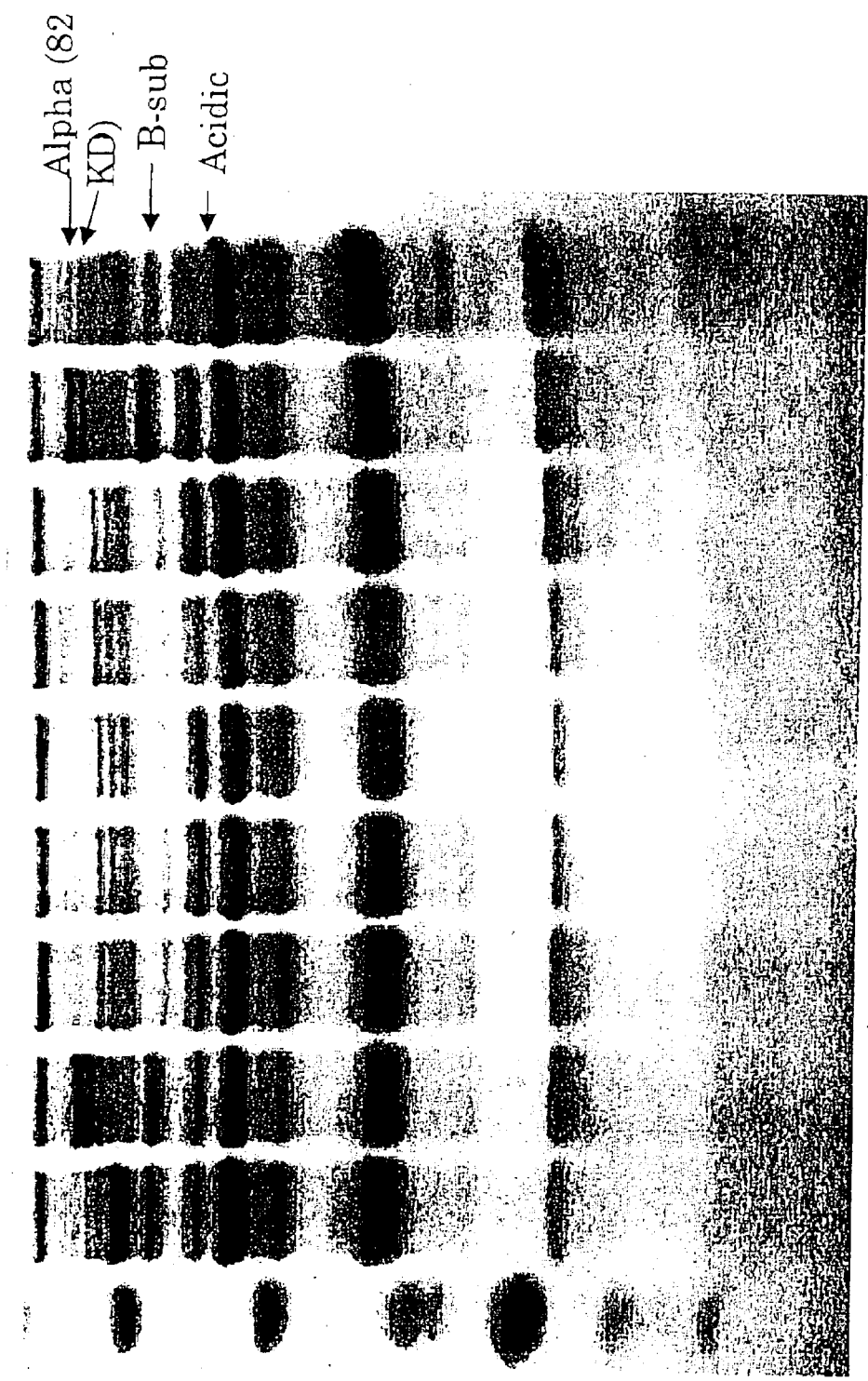

Protein samples were prepared according to standard methods from seeds of transformed plants exhibiting a co-suppression phenotype with respect to Fad2 (i.e., transgenic plants with altered soybean oil compositions). Protein sample preparation and SDS polyacrylamide gel protocols were the same as those used in WO 97/47731, cited above. A protein gel of the seed samples is shown in FIG. 3. Seed protein profiles having reduced levels of α- or α'-subunit polypeptides (lanes 3–7, and 9) always exhibited a coordinated loss. The loss of the α'-subunit was not unexpected due to the use of the promoter for the α'-subunit of beta-congylcinin. However, this promoter also appeared to suppress the accumulation of the α-subunit polypeptide as efficiently as the α'-subunit. Not all of the altered oil lines showed reduced levels of α or α' subunit (lane 8) even though all contain the beta-conglycinin promoter. Lanes 1 and 2 are a positive and negative control (respectively). Therefore, it appears that the use of the promoter for the α'-subunit of beta-conglycinin, when used in recombinant expression constructs, is sufficient to coordinately suppress both α- and α'-subunits of beta-conglycinin in soybean plants.

What is claimed is:

1. A recombinant expression construct to lower Gly m Bd 30K (Soybean vacuolar protein P34) content of a soybean which comprises a promoter operably linked to an isolated nucleic acid fragment corresponding to all or a part of SEQ ID NO:1 wherein the expression of said construct is sufficient to lower the Gly m Bd 30 K content.

2. The recombinant expression construct of claim 1 wherein the promoter is selected from the group consisting of an α'-subunit beta-conglycinin promoter, a Kunitz Trypsin Inhibitor (KSTI) promoter, a Gly m Bd 28K promoter, T7 promoter, a 35S promoter and a beta-phaseolin promoter.

3. A recombinant expression construct to lower the Gly m Bd 30K (Soybean vacuolar protein P34) content of a soybean which comprises a beta-conglycinin promoter operably linked to an isolated nucleic acid fragment corresponding to all or a part of SEQ ID NO:1 wherein the expression of said construct is sufficient to lower the Gly m Bd 30 K content.

4. A soybean plant comprising in its genome at least one of the expression constructs of any of claim 1, 2, or 3.

5. A seed of the plant of claim 4 wherein said seed comprises the expression construct of claim 1.

* * * * *